United States Patent
Attariwala et al.

(10) Patent No.: US 11,092,569 B1
(45) Date of Patent: Aug. 17, 2021

(54) APPARATUS AND METHODS FOR DETECTION OF MOLECULES

(71) Applicant: CANNABIX TECHNOLOGIES INC., Burnaby (CA)

(72) Inventors: Rajpaul Attariwala, Vancouver (CA); Daryoush Sahebjavaher, West Vancouver (CA); Jared Boock, Gainesville, FL (US); Mikko Maatta, Vancouver (CA)

(73) Assignee: CANNABIX TECHNOLOGIES INC., Burnaby (CA)

( * ) Notice: Subject to any disclaimer, the term of this patent is extended or adjusted under 35 U.S.C. 154(b) by 0 days.

(21) Appl. No.: 17/019,728

(22) Filed: Sep. 14, 2020

Related U.S. Application Data

(60) Provisional application No. 63/048,149, filed on Jul. 5, 2020.

(51) Int. Cl.
| | |
|---|---|
| *G01N 27/624* | (2021.01) |
| *H01J 49/24* | (2006.01) |
| *G01N 33/497* | (2006.01) |
| *H01J 49/06* | (2006.01) |

(52) U.S. Cl.
CPC ......... *G01N 27/624* (2013.01); *G01N 33/497* (2013.01); *H01J 49/067* (2013.01); *H01J 49/24* (2013.01)

(58) Field of Classification Search
CPC .... G01N 27/624; G01N 27/64; G01N 27/622; H01J 49/165; H01J 49/0018; H01J 49/049; H01J 49/0404
See application file for complete search history.

(56) References Cited

U.S. PATENT DOCUMENTS

| | | |
|---|---|---|
| 6,495,823 B1 | 12/2002 | Miller et al. |
| 6,512,224 B1 | 1/2003 | Miller et al. |
| 7,057,168 B2 | 6/2006 | Miller et al. |

(Continued)

FOREIGN PATENT DOCUMENTS

| | | |
|---|---|---|
| CA | 2502445 C | 8/2011 |
| WO | 2000/008455 A1 | 2/2000 |

(Continued)

OTHER PUBLICATIONS

R. Yost, Enhanced Selectivity and Sensitivity in FAIMS. Department of Chemistry, University of Florida, Pittcon Presentation, Mar. 14, 2011.

(Continued)

*Primary Examiner* — David E Smith
*Assistant Examiner* — Hsien C Tsai
(74) *Attorney, Agent, or Firm* — Oyen Wiggs Green & Mutala LLP

(57) ABSTRACT

A system for detecting a chemical substance of interest among a plurality of different chemical substances comprises an inlet, an ionization module, a high-field asymmetric waveform ion mobility spectrometry (FAIMS) cell, and optionally a detector. A focussing module and/or a flow control gas supply can be provided. The system has example applications for molecules including Δ-9-tetrahydrocannabinol (THC), its metabolites and/or other substances of interest from a breath of a subject or from a breath sample obtained from a subject.

20 Claims, 23 Drawing Sheets

(56) References Cited

U.S. PATENT DOCUMENTS

| | | | |
|---|---|---|---|
| 8,237,118 B2 | 8/2012 | Prox et al. | |
| 2005/0161596 A1 | 7/2005 | Guevremont et al. | |
| 2008/0004542 A1 | 1/2008 | Allen et al. | |
| 2008/0017791 A1 | 1/2008 | Wilks et al. | |
| 2008/0128609 A1* | 6/2008 | Miller | G01N 27/624 250/282 |
| 2009/0032701 A1* | 2/2009 | Rodier | G01N 27/622 250/282 |
| 2012/0056085 A1* | 3/2012 | Giles | G01N 27/624 250/282 |
| 2018/0286657 A1* | 10/2018 | Welkie | H01J 49/0481 |
| 2020/0243317 A1* | 7/2020 | Lopez-Hilfiker | G01N 33/46 |

FOREIGN PATENT DOCUMENTS

| | | |
|---|---|---|
| WO | 2001/069216 A2 | 9/2001 |
| WO | 2001/069217 A2 | 9/2001 |
| WO | 2002/071053 A2 | 9/2002 |
| WO | 2017/147687 A2 | 9/2017 |

OTHER PUBLICATIONS

R. Yost et al., FAIMS/MS as an Emerging Technique for the Clinical Laboratory. University of Florida, ASMS Jun. 10, 2013.

Tsai, Keywords: FAIMS; squrewaveforms; miniaturized planar cell; explosives. ASMS Abstract 2009 Philadelphia.

Costanzo et al. Analysis of Volatile Organic Compounds in Human Breath by FAIMS/MS. University of Florida, ASMS Extended Abstract 2012.

Yost et al., Innovations in FAIMS: Geometries and Gas-phase Chemistry. Department of Chemistry, University of Florida, ACS Presentation Aug. 19, 2012.

Kero et al., Trace analysis of thiocyanate ion, a possible biomarker for cystic fibrosis, by ESI/FAIMS/MS. ASMS Abstract 2004.

Beekman, Keywords: FAIMS, DMS, microfabricated; high speed, ion mobility; tandem MS; triple quadrupole. ASMS Abstract 2013 Minneapolis.

Kero et al., Development of a novel screening method for the quality assurance of exhaled breath condensate in the clinical laboratory. Mar. 2007.

Yost et al. Conventional and Differential Ion Mobility Spectrometry. Department of Chemistry, University of Florida, Abstract 2012 ACS Philadelphia.

Kero et al., From Blood to Breath: the Detection of THC in Exhaled Breath by Adsorbent Tube LC-MS/MS. ASMS Abstract 2007.

Rorrer et al. Solvent vapor effects on planar high-field asymmetric waveform ion mobility spectrometry. International Journal of Mass Spectrometry, Mar. 2011.

Barnett et al. Characterization of a Temperature-Controlled FAIMS System. J. Am Soc. Mass Spectrom. 2007, 18, 1653-1663.

Shvartsburg et al. Optimum Waveforms for Differential Ion Mobility Spectrometry. J. Am Soc. Mass Spectrom. Sep. 2009.

* cited by examiner

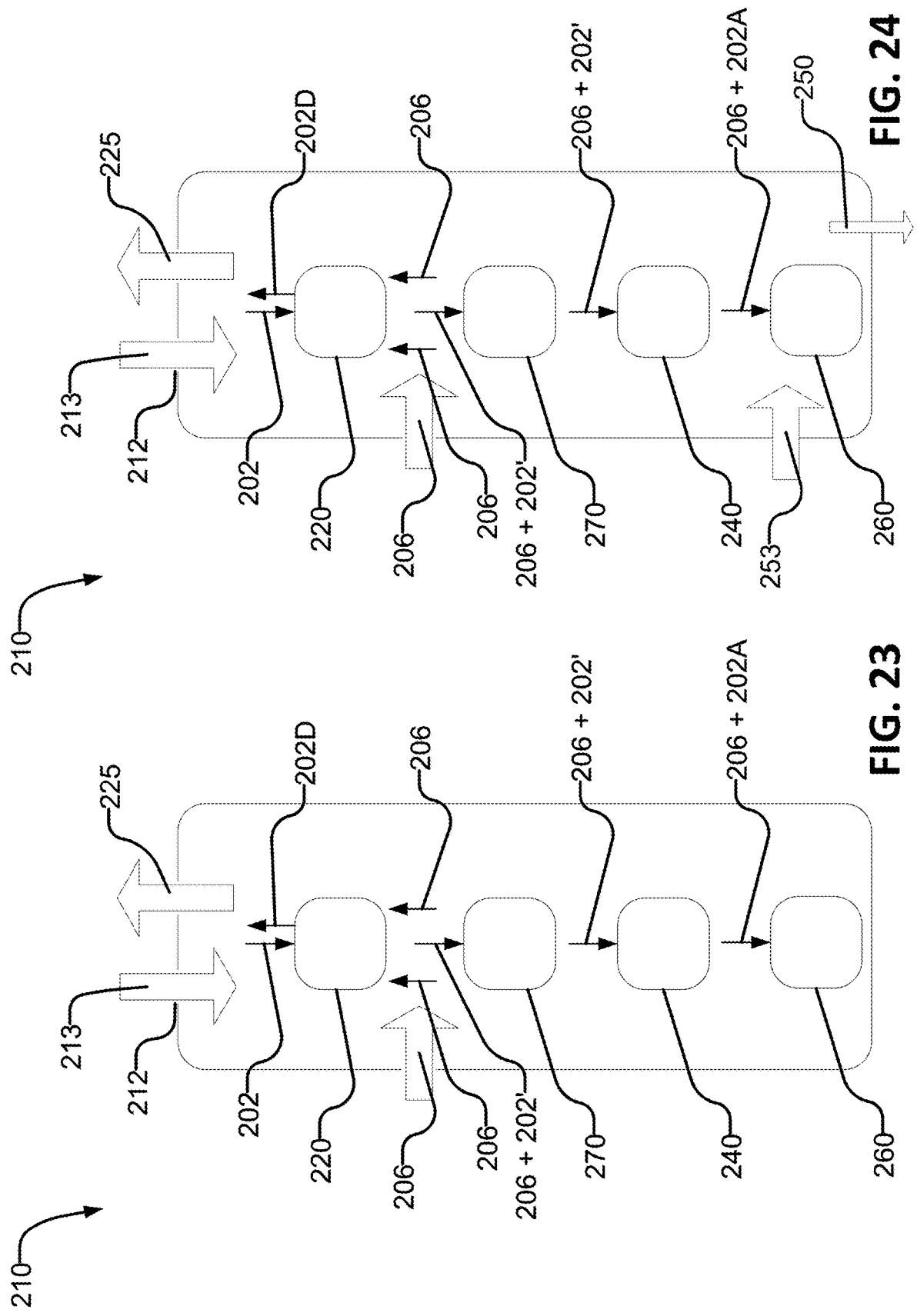

APPARATUS AND METHODS FOR DETECTION OF MOLECULES

CROSS-REFERENCE TO RELATED APPLICATIONS

This application claims the benefit under 35 U.S.C. § 119 of U.S. Application No. 63/048,149 filed 5 Jul. 2020 and entitled APPARATUS AND METHODS FOR DETECTION OF MOLECULES which is hereby incorporated herein by reference in its entirety for all purposes.

TECHNICAL FIELD

Some embodiments of this invention relate to field asymmetric ion mobility spectrometry (FAIMS) systems. Particular embodiments have example applications for detecting one or more substances (including e.g. tetrahydrocannabinol) from the breath of a subject.

BACKGROUND

The legalization of marijuana in many locations around the world has resulted in a need for novel devices which can detect recency of use of cannabis. Current methods employed to collect and analyze use of cannabis include blood draw and urinalysis. These methods are invasive to the subject and time-consuming.

Tetrahydrocannabinol (THC) is the principal psychoactive constituent of cannabis. Due to its unique molecular properties, detection of THC is not as straightforward as detection of other analytes of interest such as alcohol. There is a general desire for non-invasive methods which can detect compounds, such as THC, from cannabis.

High-field asymmetric waveform ion mobility spectrometry (FAIMS) is a highly selective means of separating ions by shape-to-charge at atmospheric pressure. FAIMS involves exposing ions to a high electric field to cause the ion mobility (e.g. the movement of ions in an electric field) of different types of ions to change differently. Different types of ions can be resolved from each other based on their ion mobilities and/or changes in ion mobility in the presence of the high electric field.

A FAIMS device (e.g. a FAIMS cell) typically consists of a first electrode driven by an asymmetric waveform and a second grounded electrode. Driving the first electrode with an asymmetric waveform creates a time varying electric field which causes ions flowing through a region between the first and second electrodes to oscillate between the first and second electrodes. The first electrode is driven by a waveform which is typically one or more combinations of sums-of-sines to approximate a square wave.

One issue with driving a FAIMS cell with an approximation of a square wave is that it introduces delay (i.e. lag time) to the ion oscillations, thereby causing the FAIMS cell to have low efficiency, low resolving power and large device footprint. Another issue with some FAIMS cells is that they not are electrically isolated and are susceptible to electrical interferences. Another issue with some FAIMS cells is that they are not thermally isolated or capable of being maintained at a constant temperature, thereby lowering resolving power.

There is a general desire to provide FAIMS cells which overcome the above-noted shortcomings. There is a general desire to provide FAIMS-based detection systems having greater sensitivity and/or specificity for detection of a desired molecule such as THC.

The foregoing examples of the related art and limitations related thereto are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

One aspect of the invention relates to a system for detecting a target substance among multiple substances released from a source. The system comprises an inlet for receiving the substances from the source, an ionization module, a focusing module positioned downstream of the ionization module, and a FAIMS cell positioned downstream of the focusing module. The ionization module is operative to ionize at least some of the substances received through the inlet to produce ionized substances that travel along a linear flow path from a point where the ionized substances are ionized. The focusing module is configured to guide the ionized substances to travel along the linear flow path to the FAIMS cell. The FAIMS cell has an entry positioned along the linear flow path.

In some embodiments, the linear flow path travelled by the ionized substances produced by the system, from the point where the plurality of ionized substances are ionized to the FAIMS cell, follows a principle axis. In some embodiments, the inlet, the ionization module, the focussing module and the FAIMS cell are linearly aligned along the principle axis.

In some embodiments, the focusing module comprises one or more focussing electrodes capable of exerting a radial component of electromagnetic force on the ionized substances. In some embodiments, the focusing module comprises a magnetic lens. In some embodiments, the focusing module comprises an apparatus for exerting pneumatic and/or aerodynamic focussing forces.

In some embodiments, the system further comprises a gas inlet port positioned upstream of the FAIMS cell for introducing a flow control gas into the system to regulate a rate of fluid flow upstream of the FAIMS cell. The gas inlet port may be provided at the focusing module. A vacuum source may be provided to draw air in a downstream direction through the system. In some embodiments, the flow control gas is introduced into the system at a rate which is equal to a suction rate of the vacuum. In other embodiments, the flow control gas is introduced into the system at a rate which is greater than a suction rate of the vacuum. In some embodiments, the system further comprises an outlet positioned upstream of the gas inlet port to allow unionized substances to exit the system. In some embodiments, the system further comprises a second gas inlet port for introducing a further portion of the flow control gas into the system. The second gas inlet port may be positioned downstream of the FAIMS cell and upstream of a detector.

In some embodiments, the FAIMS cell is a planar FAIMS cell. The planar FAIMS cell may comprise first and second electrodes spaced by a gap to define a transit area therebetween. The transit area may have opposing sides which define the entry and an exit of the planar FAIMS cell. The planar FAIMS cell may comprise a first voltage source coupled to the first electrode and operative to drive the first electrode with a first waveform, and a second voltage source coupled to the second electrode and operative to drive the second electrode with a second waveform. The first and second waveforms may be controlled to generate a time varying electric field in the transit area to separate the target substance from other substances as the ionized substances travel from the entry to the exit of the planar FAIMS cell such that primarily or only the target substance exits the planar FAIMS cell. The first and second waveforms may combine to result in the production of a net square waveform.

Another aspect of the invention relates to a method of separating substances using FAIMS. The method comprises introducing the substances into an inlet followed by passing the substances past an ionization module to ionize at least some of the substances. The ionized substances are then caused to travel along a linear flow path from a point where the substances are ionized to a focusing module. Forces provided by the focusing module are then used to guide the ionized substances along the linear flow path towards a FAIMS cell. The FAIMS cell is then used to separate the ionized substances.

In some embodiments, the forces provided by the focusing module comprise magnetic, pneumatic and/or aerodynamic forces. In some embodiments, the forces provided by the focusing module comprise electromagnetic forces. The forces provided by the focusing module may comprise a radial component of electromagnetic force produced by the focusing electrode.

In some embodiments, the method comprises using a planar FAIMS cell to separate the ionized substances. The path of travel of the ionized substances through the FAIMS cell may be along the linear flow path. In some embodiments, separation of the ionized substances by the planar FAIMS cell is effected using a net square waveform.

In some embodiments, the method further comprises using the introduction of a flow control gas downstream of the ionization module to force at least some of the unionized portion of the substances out of the flow path through an outlet.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

FIG. 23 is a schematic view of a system for detecting target substances according to an example embodiment.

FIG. 24 is a schematic view of a system for detecting target substances according to an example embodiment.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

Figure 1:
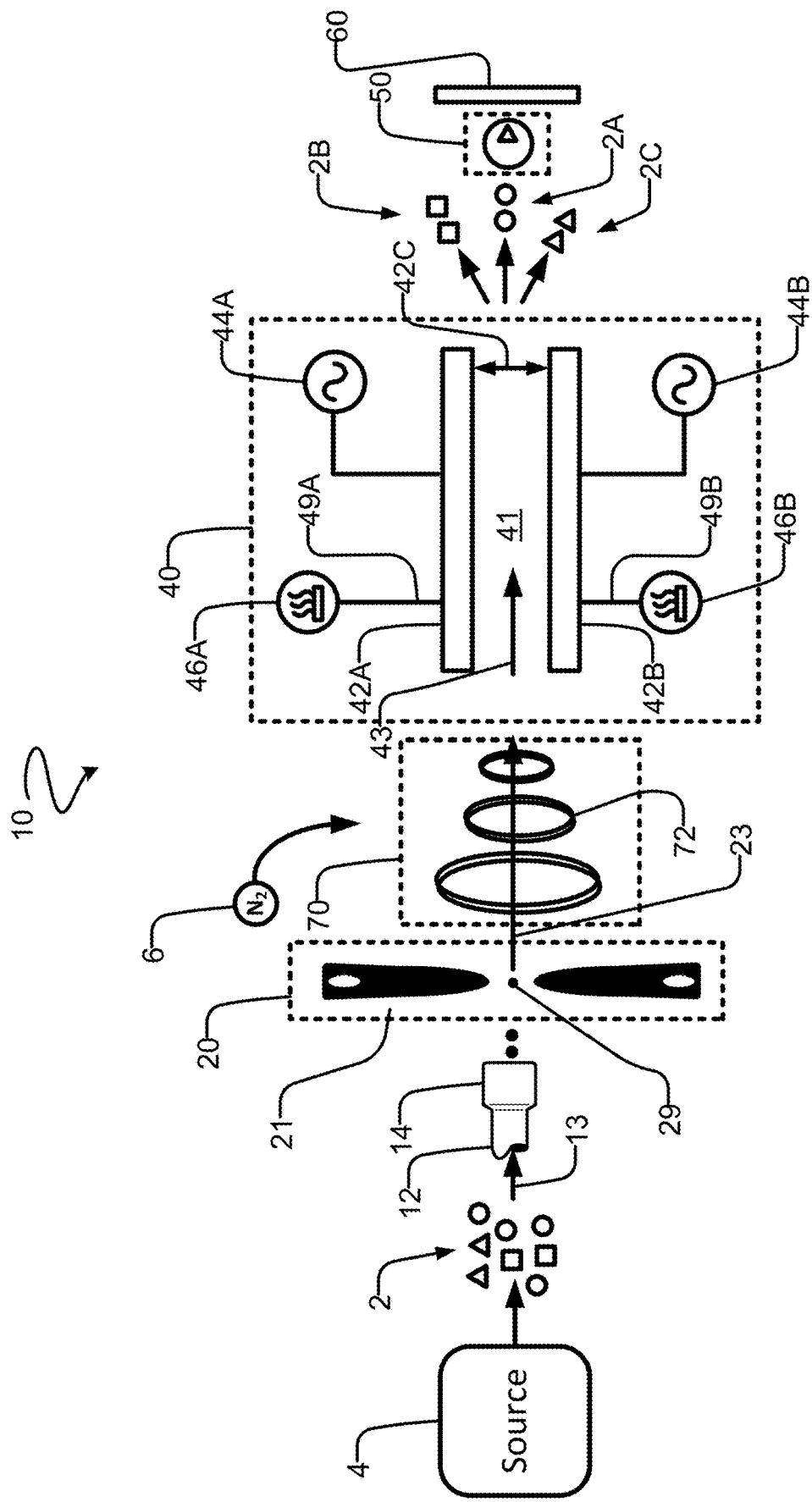
FIG. 1 is a schematic diagram of a system for detecting a chemical substance of interest according to an example embodiment.

FIG. 1 is a schematic diagram of an example system 10 for detecting a chemical substance of interest 2A (i.e. a target substance) among a plurality of different chemical substances 2 released from a source 4. System 10 has example applications for detecting one or more components of a controlled substance from a breath of a subject (i.e. a person suspected of having consumed a controlled substance). For example, system 10 may have applications for detecting tetrahydrocannabinol (THC) and/or other psychoactive components of cannabis from a breath of a subject. System 10 can be used to detect any molecule or combination of molecules that can be detected using FAIMS, including for example other drugs or metabolites, biomarkers of various disease states, bacterial or viral pathogens, or the like.

For these applications, system 10 may be incorporated into a portable system such as a handheld breathalyzer which can detect consumption of a controlled substance (e.g. cannabis) in real time. System 10 may alternatively be provided in a laboratory setting. Where system 10 is incorporated into a portable system, source 4 may be a subject exhaling breath containing substances 2 directly into an inlet 12 of system 10 (e.g. see FIG. 13). Where system 10 is provided in a laboratory setting (or in a field setting if desired), source 4 may be a cartridge storing a sample of a breath of a subject containing substances 2 (e.g. see FIG. 14).

The above examples of source 4 are not exhaustive. Source 4 may generally comprise any source of fluids. In a currently preferred embodiment, system 10 is configured to detect a target substance 2A from a source 4 which releases aerosolized substances, for example as contained in breath or as released from collected breath condensates previously obtained and stored in a sample container.

As depicted in FIG. 1, system 10 comprises an inlet 12 for receiving an inlet flow, represented by arrow 13, containing substances 2 from source 4, an ionization module 20 for ionizing substances 2 drawn into system 10, a field asymmetric ion mobility spectrometry (FAIMS) cell 40 for separating the ionized substances 2 according to their ionic mobility and/or mass, vacuum and/or pump means 50 for moving substances 2 through cell 40, and one or more detectors 60 for detecting one or more of the separated substances (e.g. substances 2A, 2B, 2C as shown in FIG. 1).

Any suitable detector can be used as detector 60, for example, a Faraday cup detector, single plate detector, metal oxide sensor, chemical detector including a chemical reaction, conformational change in a detecting substance and/or chemical adsorption triggered by or sensitive to the substance of interest, or the like. In some embodiments, using a chemical detector sensitive to the substance of interest can help to magnify the signal produced by the system for detection, to increase sensitivity of the system. In some embodiments, detector 60 is omitted and system 10 is connected instead to any suitable analytic device, for example a mass spectrometer, to carry out analysis on substances that pass through FAIMS cell 40.

As used herein, the terms "upstream" and "downstream" are used with reference to the direction flow of substances 2 through system 10. As an example, inlet 12 is upstream of ionization module 20, while FAIMS cell 40 is downstream of focussing module 70.

In some embodiments, system 10 comprises a means for introducing a flow control gas 6 into system 10. Flow control gas 6 may comprise nitrogen gas or the like. Flow control gas 6 is typically introduced into system 10 downstream of ionization module 20 and upstream of FAIMS cell 40. In some embodiments, flow control gas 6 is provided upstream of focussing module 70 but downstream of ionization module 20 and/or downstream of focussing module 70 but upstream of FAIMS cell 40. Flow control gas 6 may be provided to replace unwanted moisture in the fluid carrying substances 2 and/or act as a carrier gas which carries substances 2 through cell 40, as explained in greater detail below.

In some embodiments, system 10 comprises a focussing module 70 designed to help guide the ionized substances 2 into a transit area 41 of FAIMS cell 40 in a desirable manner as described in greater detail below. Focussing module 70 is typically located between ionization module 20 and cell 40.

Figure 2:
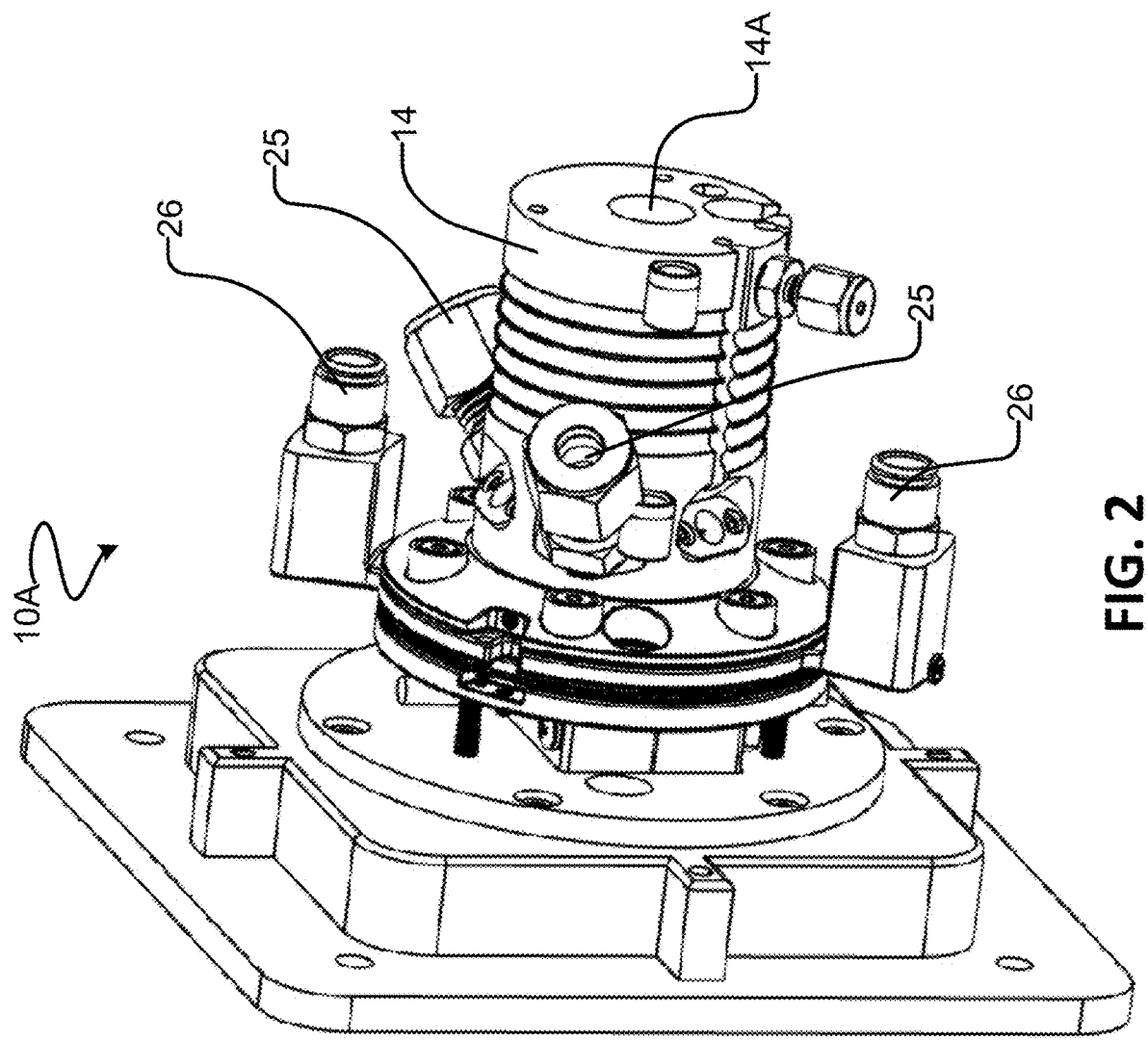
FIG. 2 is a perspective view of an exemplary system for detecting a chemical substance of interest.
Figure 3:
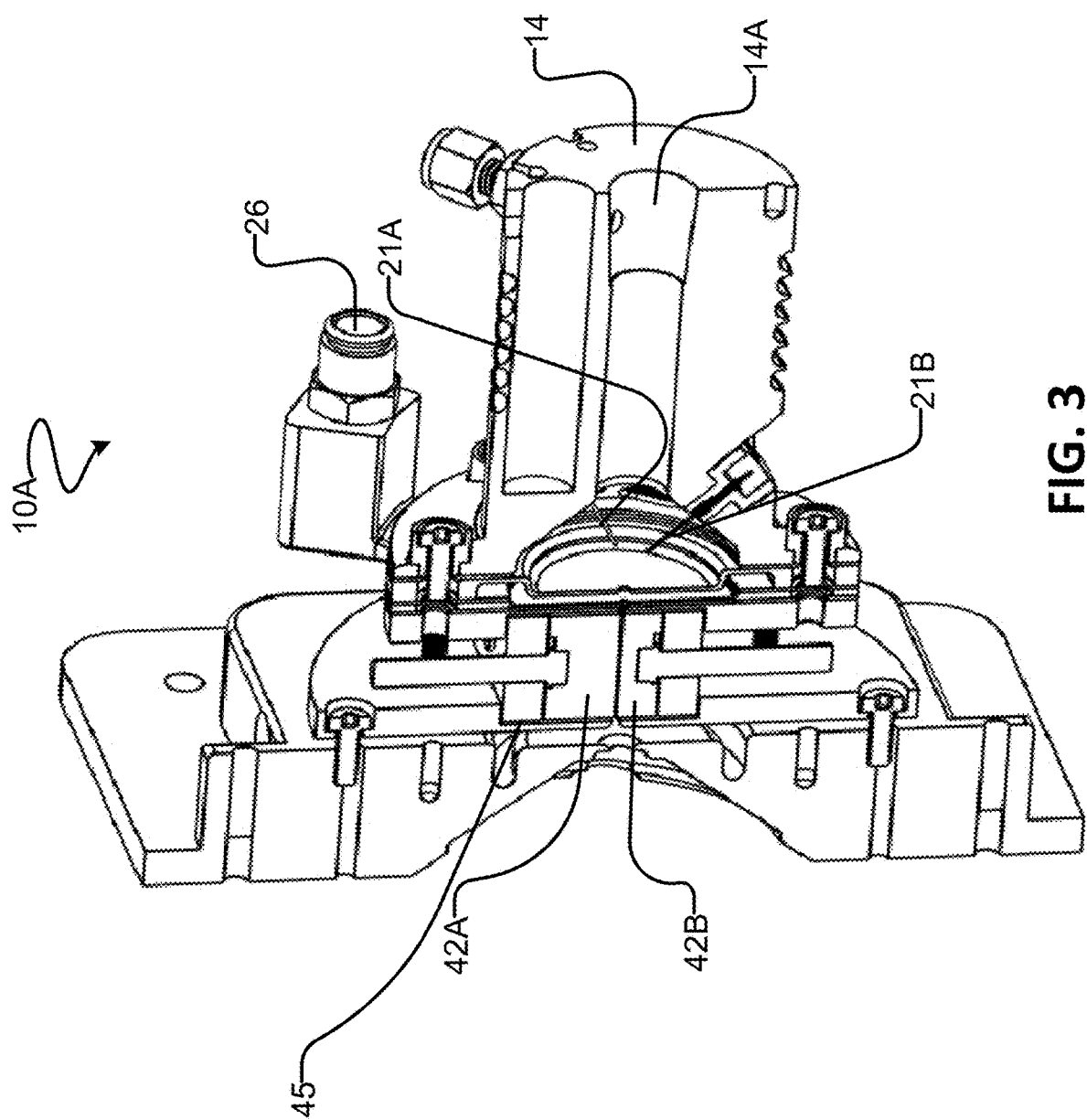
FIG. 3 is a perspective sectional view of the FIG. 2 system.

FIG. 2 is a perspective view of an example embodiment of system 10A which may be used to detect a THC target substance 2A from a breath of a subject containing substances 2. As depicted in FIGS. 2-6, system 10A comprises a tube 14 located between inlet 12 (see FIG. 1) and ionization module 20. Tube 14 is typically elongated. Tube 14 has a length extending in its direction of elongation which is typically in the range of about 2 cm to about 10 cm (including any value therebetween, e.g. 3, 4, 5, 6, 7, 8 or 9 cm). Tube 14 has a bore 14A extending therethrough to define a corresponding conduit which allows substances 2 to flow from inlet 12 downstream to ionization module 20. Tube 14 may be integrally formed with inlet 12 (e.g. inlet 12 may be provided at an end portion of tube 14).

Tube 14 may be made of any suitable material. In one embodiment, tube 14 including bore 14A is made of stainless steel (e.g. SS316), which is thermally and electrically conductive and corrosion resistant. In other embodiments, tube 14 including bore 14A is made of aluminum. In some embodiments, bore 14A is coated with a material having desired properties, e.g. glass, silica and/or gold, and/or material with hydrophobic or hydrophilic properties.

In some embodiments, tube 14 is heated to an elevated temperature which is typically in the range of about 50° C. to about 300° C. (including any value therebetween, e.g. 75, 100, 125, 150, 175, 200, 225, 250 or 275° C.) to increase the temperature of substances 2 as substances 2 flow from inlet 12 downstream to ionization module 20. Any suitable mechanism can be used to heat tube 14, e.g. a heating jacket, appropriately positioned thermally conductive heating wires, or the like.

Ionization module 20 may be any suitable ionization source operative to ionize substances 2. Ionization module 20 typically ionizes substances 2 to a single polarity (i.e. positive or negative). For example, ionization module 20 may have one or more corona discharge needles 21 operative to ionize substances 2 to a single polarity. The ionization energy (e.g. the voltage applied to needles 21) is typically in the range of 2,500V to 3,000V although voltages outside of this range are possible. The ionization energy may be adjusted in some cases to create different types of ionized substances 2 (i.e. the mass to charge ratio of ionized substances 2 may be adjusted based on the ionization energy).

In the example embodiment illustrated in FIGS. 2-7, system 10A comprises three corona discharge needles 21A, 21B, 21C. In some embodiments, the corona discharge needles are 21A, 21B, 21C arranged in a cone-like structure (e.g. see FIG. 7). In some embodiments, the corona discharge needles 21A, 21B, 21C in system 10A are evenly spaced circumferentially to form an azimuthal angle of about 120° between adjacent corona discharge needles 21A, 21B, 21C. In some embodiments, the corona discharge needles 21A, 21B, 21C in system 10A are each oriented to form a polar angle of about 30° to 60° relative to a central axis of tube 14. In some embodiments, the corona discharge needles 21A, 21B, 21C are oriented to point to a common location along the central axis of tube 14.

Figure 4:
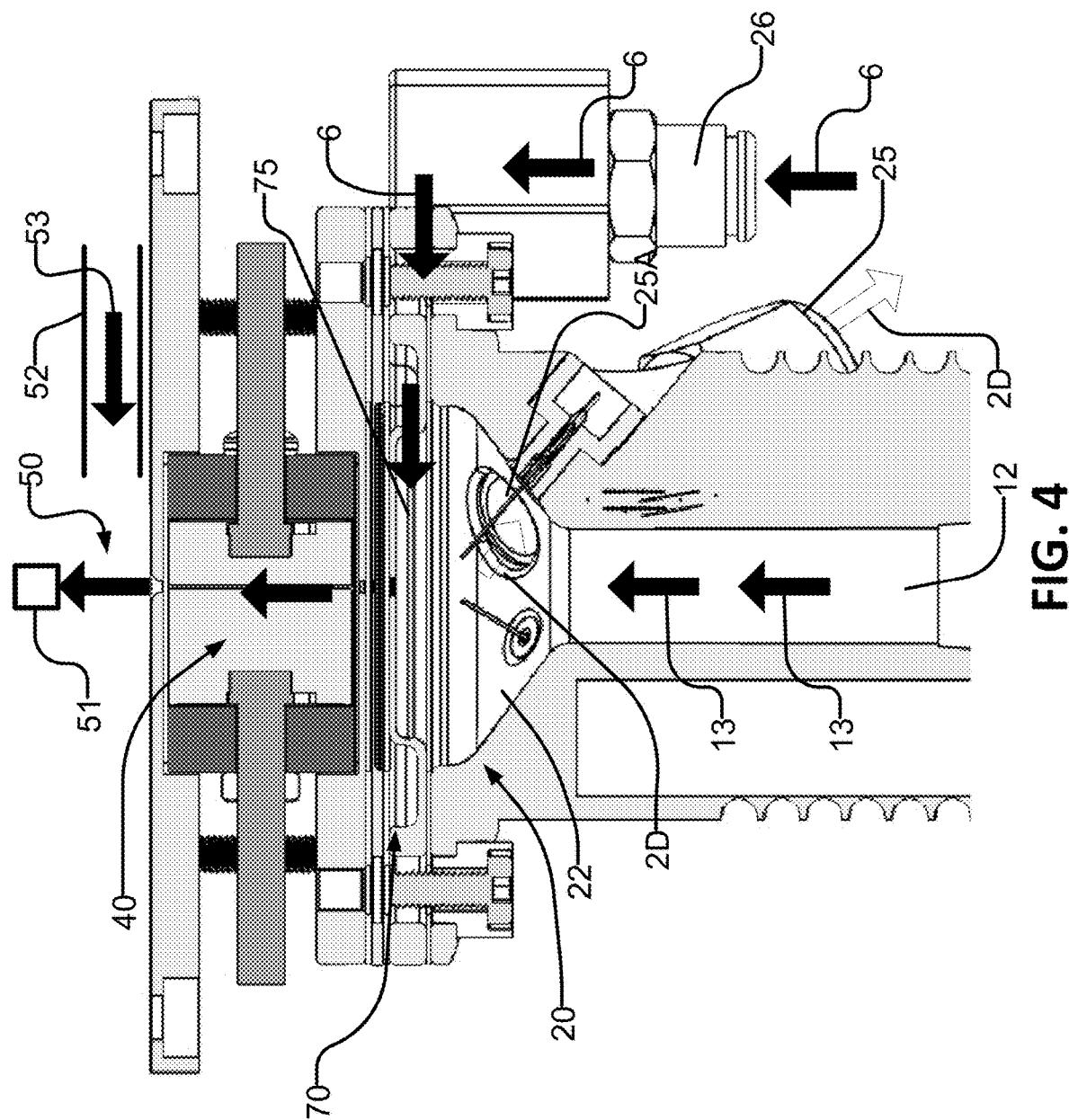
FIG. 4 is a cross-sectional view of the FIG. 2 system.

Without being bound by theory, the use of a plurality of symmetrically disposed corona discharge needles as aforesaid may assist in creating a directional field in which anything passing through such field is ionized. Inlet flow 13 may be in the nature of an airflow having a generally circular cross-section, and it is desirable that as many substances 2 as possible are ionized when passing through the ionization module 20. To achieve this, in some embodiments the ionization units such as corona discharge needles 21A, 21B, 21C are offset from (i.e. do not extend into or through) the central axis of inlet flow 13, as best seen in FIG. 4. To maintain symmetry to increase as much as possible the concentration of ions in the ionization field, a plurality of ionization sources disposed in an offset and symmetrical manner about the central axis of inlet flow 13, as described for corona discharge needles 21A, 21B, 21C. Providing a plurality of ionization sources in a symmetrically disposed configuration but offset from the path of inlet flow 13 may help increase the ionization of substances 2 while minimizing undesirable effects of the presence of the ionization sources on the flow of substances 2.

In alternative embodiments, ionization module 20 may be other types of ionization sources such as: electrospray ionization, radioactive ionization, photoionization, desorption ionization (e.g. laser), dielectric barrier discharge (DBD), suitable ionization filaments and the like.

In some embodiments, a sheath gas is supplied to flow around the ionization source, e.g. around needles 21A, 21B, 21C, to assist in directing molecules towards focussing module 72.

In some embodiments, including the illustrated embodiment, the introduction of ionized substances 2 into FAIMS cell 40 is done in a parallel manner. That is, the flow path 23 along which the ionized substances 2 travel after having been ionized by ionization module 20 to FAIMS cell 40 is linear. This parallel injection can be contrasted with the orthogonal injection more typically used for FAIMS systems.

In some embodiments, including the illustrated embodiment, the injected sample flows along the same linear axis through all of inlet 12, ionization module 20, focussing module 70 and FAIMS cell 40, e.g. both inlet flow 13 and fluid flow path 43 extend along the same axis, which can be referred to as a principle axis.

In alternative embodiments, tube 14 can be positioned and configured so that inlet 12 is oriented in any desired direction, e.g. in a direction orthogonal to the principle axis, and the ionization module 20 can be provided with any desired orientation and location, as long as the flow path 23 for ionized substances downstream of the point 29 where they are ionized to the point where the ionized substances 2 enter FAIMS cell 40 (including passing through focussing module 70) is linear. [0068] In the example embodiment shown in FIG. 2, system 10A comprises one or more exhausts 25 provided proximate ionization module 20 to allow for removal of unionized and/or undesired substances 2D (e.g. moisture droplets) out of system 10A. In some embodiments, exhaust 25 is in direct fluid communication with the external atmosphere. In some embodiments, exhaust 25 is in fluid communication with a vacuum or a pump which can help expel unionized substances 2 (e.g. droplets) out of system 10A.

Figure 5:
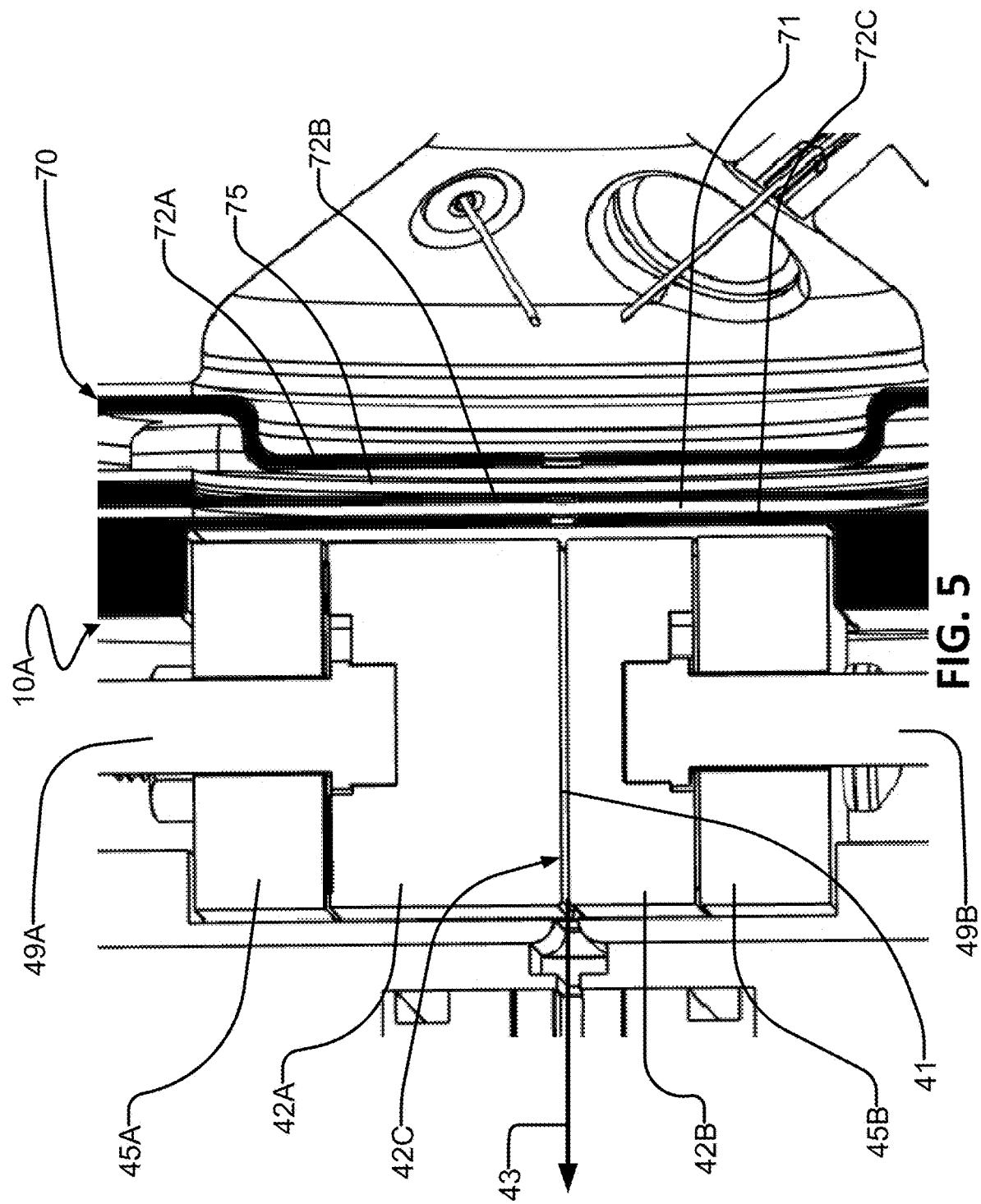
FIG. 5 is a side sectional view of a FAIMS cell of the FIG. 2 system.
Figure 6:
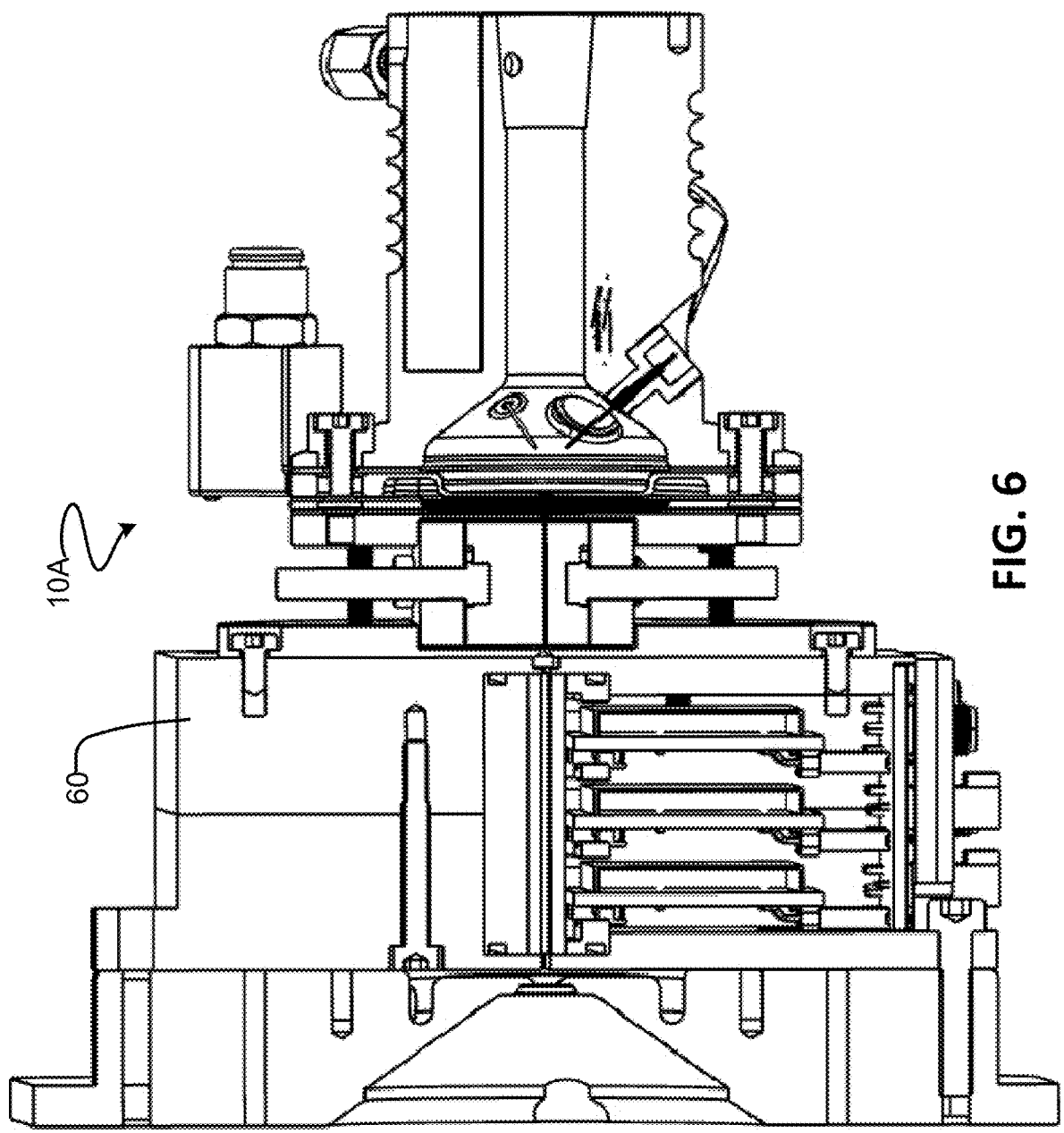
FIG. 6 is a side sectional view of the FIG. 2 system.
Figure 7:
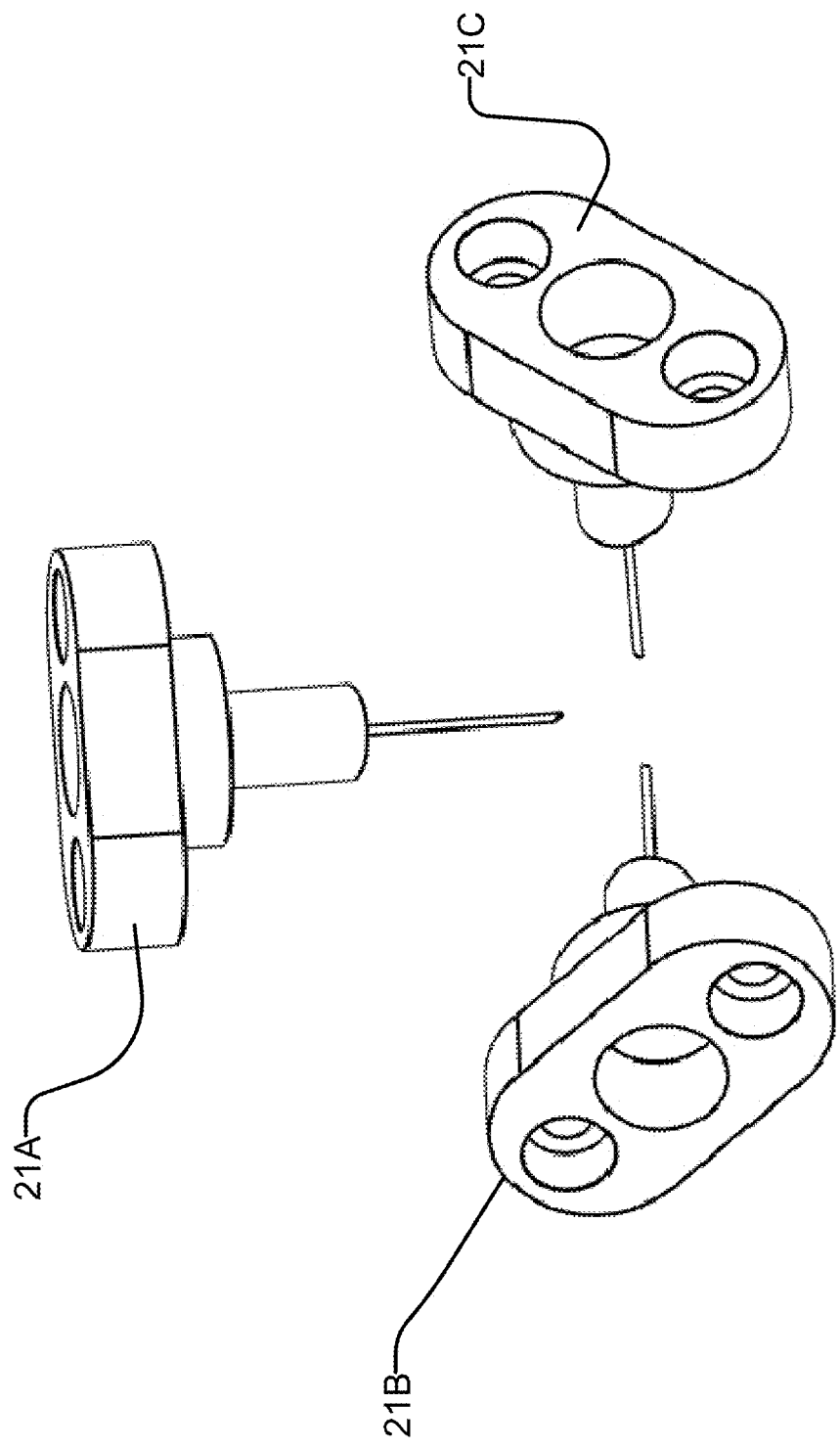
FIG. 7 is a perspective view of an ionization module of the FIG. 2 system.

In the view shown in FIG. 4, the flow of flow control gas 6 through focussing module 70 is illustrated with dark solid arrows labelled as 6. Flow control gas 6 is supplied through at least one inlet port 26, which is in fluid communication with an interior space 75 defined between adjacent ones of the focussing electrodes 72 in focussing module 70 (FIG. 5). Suction provided by vacuum means 50 draws flow control gas 6 from within focussing module 70 towards FAIMS cell 40, drawing with it any ionized substances 2 that become entrained therein. In some embodiments, vacuum means 50 is omitted and substances 2 are drawn through system 10A only using flow control gas 6 and electrostatic forces. In some embodiments, vacuum means 50 is omitted and substances 2 are pumped through system 10A via a pressurized or atmospheric gas provided through inlet 12 (e.g. substances 2 are pumped through system 10A via inlet flow 13). In such embodiments, the flow of substances through the system can be further regulated by flow control gas 6 and/or 53 as further described herein.

In some embodiments, the flow rate of flow control gas 6 into focussing module 70 is approximately the same as the flow rate caused by vacuum means 50, so that there is no or low airflow experienced by ionized substances 2 until the ionized substances 2 enter focussing module 70. In some embodiments, the flow rate of flow control gas 6 into focussing module 70 is slightly less than the flow rate caused by vacuum means 50, so that substances 2 experience a slight airflow (e.g. of about 0.1 L/min in the downstream direction in some embodiments) prior to entering focussing module 70, to help draw the ionized substances 2 into focussing module 70. In some embodiments, the flow rate of flow control gas 6 into focussing module 70 is slightly greater than the flow rate caused by vacuum means 50, so that only ionized substances 2 can be drawn into FAIMS cell 40 through focussing module 70 via electrostatic forces, while unionized substances will be carried with flow control gas 70 out of exhaust 25. E.g. in some embodiments substances 2 experience a slight airflow (e.g. of about 0.1 L/min in the upstream direction) prior to entering focussing module 70, to help force unionized substances out of exhaust 25.

As best seen in FIG. 4, in some embodiments the inner intake 25A of exhaust 25 is provided slightly upstream of ionization chamber 22. As shown by the arrows in black outline, this allows unionized substances and undesired substances (such as moisture in breath) to exit through exhaust 25 rather than being drawn into focussing module 70, without drawing ionized substances 2 out of ionization chamber 22 together therewith. In other embodiments, inner intake 25A of exhaust 25 is provided downstream of ionization chamber 22 and upstream of focussing module 70. In some embodiments, inner intake 25A of exhaust 25 is provided at a location which is relatively proximate to needles 21.

In some embodiments, vacuum means 50 comprises a vacuum 51 which draws substances at a constant rate. In some embodiments, a second flow control gas inlet 52 operative to introduce a second flow control gas 53 into system 10 is provided downstream of FAIMS cell 40 to further control the rate of transit of substances 2 through FAIMS cell 40. For example, the second flow control gas inlet 52 may comprise valves which control the amount of second flow control gas 53 being drawn by the vacuum to control the effective flow rate caused by vacuum means 50 within FAIMS cell 40, for example by decreasing the effective vacuum flow rate within FAIMS cell 40. For example, this may help to increase the residence time of substances 2 within FAIMS cell 40, thereby maximizing the number of cycles of electric field variation that such substances are exposed to and enhancing separation. In some embodiments, the amount of flow control gas 6 and the amount of second flow control gas 53 entering system 10 are adjusted together to control the amount of airflow entering focussing module 70 and/or FAIMS cell 40, and in some such embodiments, vacuum means 50 could be omitted and the flow rate of fluid through the system could be regulated only by the rate of supply of flow control gas 6, the rate of supply of second flow control gas 53 and/or the rate of flow of substances 2 at inlet 12 (i.e. the rate of inlet flow 13).

In use, a source 4 containing substances 2 to be separated is introduced into ionization module 20 through inlet 12. As source 4 enters inlet 12, source 4 is heated, e.g. to a temperature in the range of between about 100° C. and about 350° C., including any value therebetween, e.g. 120, 140, 160, 180, 200, 220, 240, 260, 280, 300, 320 or 340° C. As source 4 enters ionization chamber 22, the fluid flow caused by vacuum means 50 and/or the electrostatic force created by focussing module 70 draws ionized substances 2 towards focussing module 70. As substances 2 enter focussing module 70, they become entrained in flow control gas 6. Meanwhile, undesired substances 2D from source 4, e.g. moisture droplets from breath if source 4 is a direct breath sample or stored sample obtained from breath, or unionized substances, are permitted to leave ionization chamber 22 via exhaust ports 25.

Figure 13:
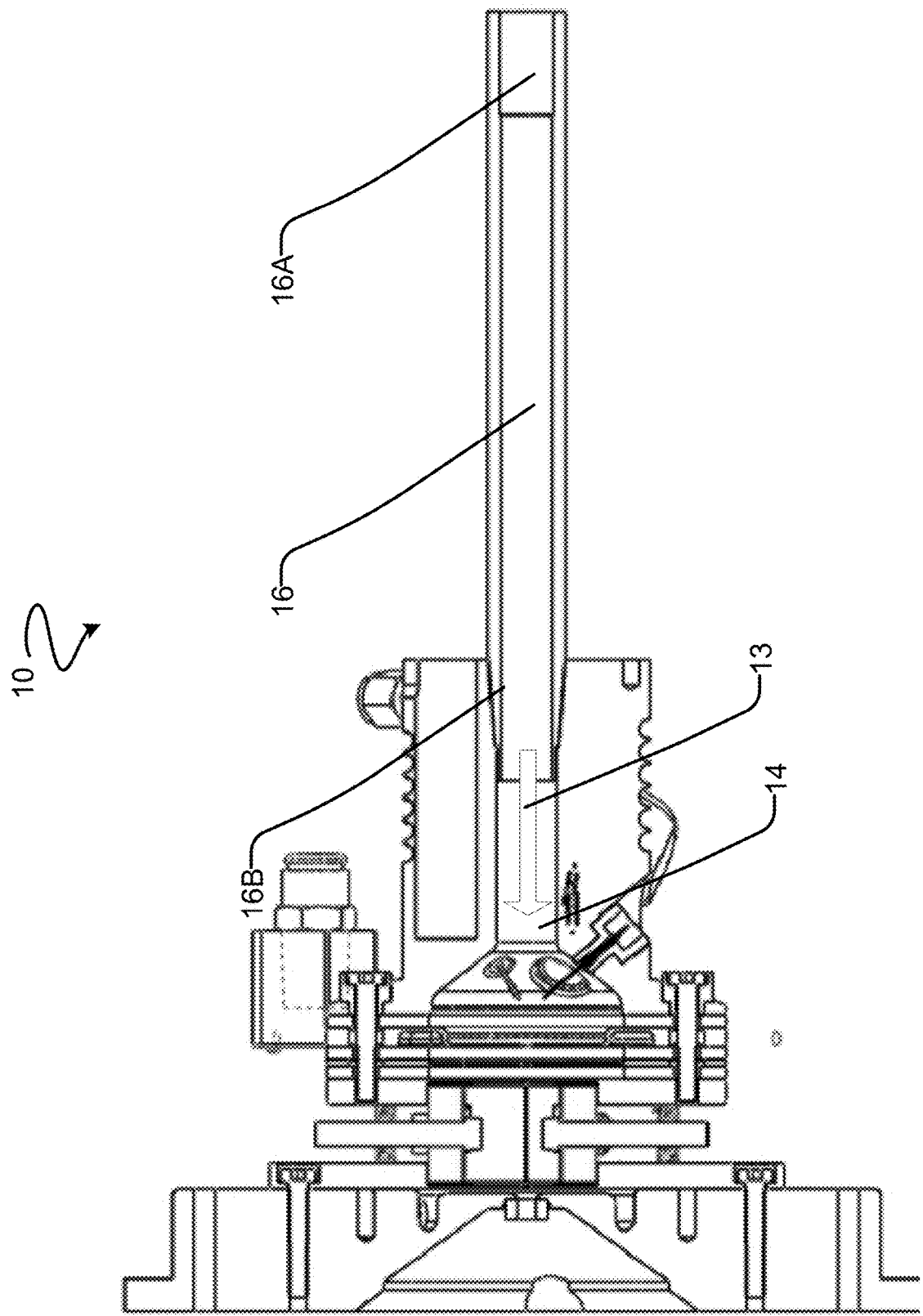
FIG. 13 is a side view of an example embodiment of a system for detecting a chemical substance of interest directly from the breath of a subject.

With reference to FIG. 13, an example embodiment of system 10 incorporating a breath inlet tube 16 is illustrated. A person can blow directly into the upstream end 16A of breath inlet tube 16, and breath flows through breath inlet tube 16 out outlet end 16B and into tube 14 of system 10 as inlet flow 13.

Figure 14:
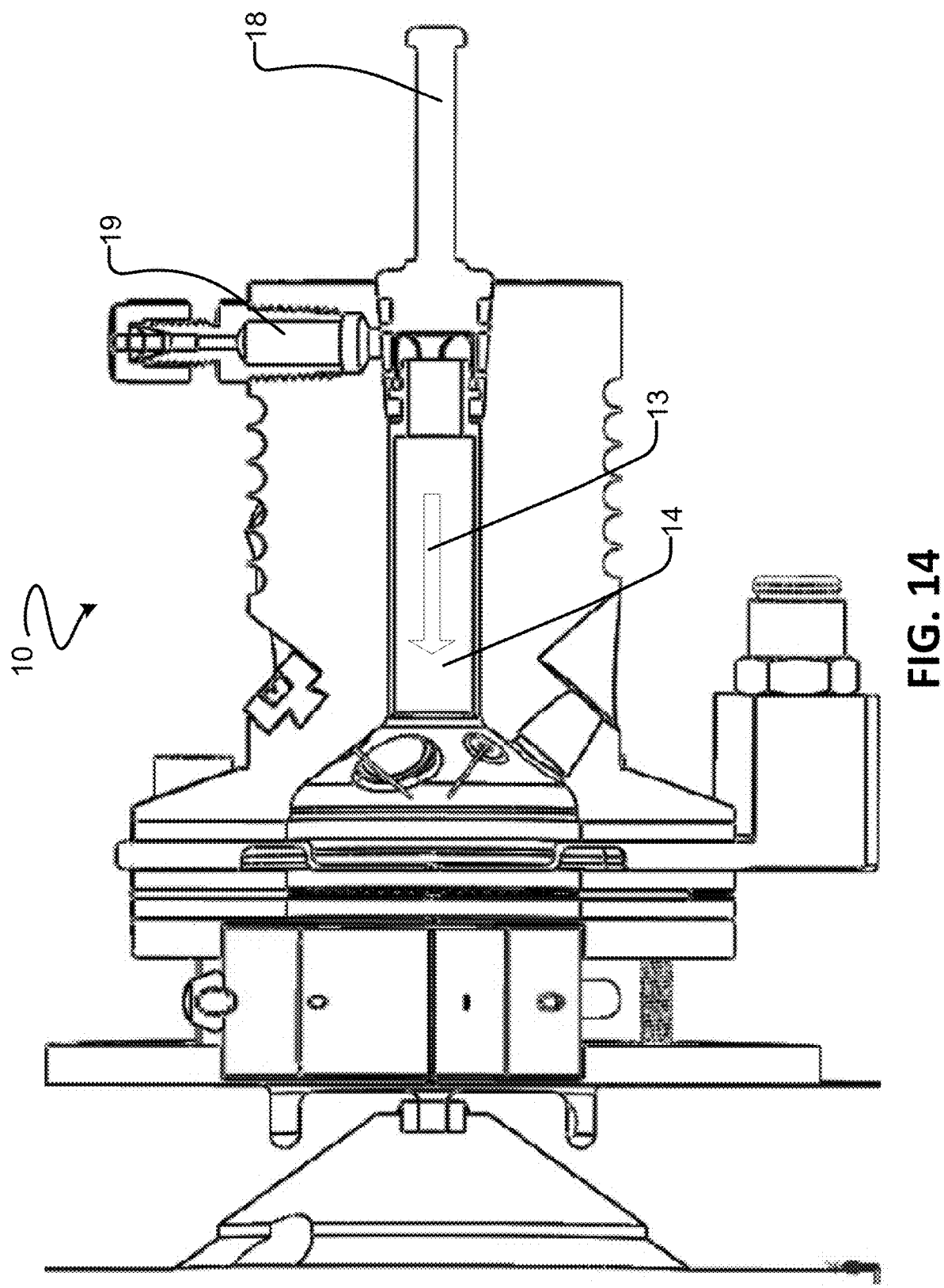
FIG. 14 is a side view of an example embodiment of a system for detecting a chemical substance of interest directly from the breath of a cartridge.

With reference to FIG. 14, an example embodiment of system 10 incorporating a breath collection tube 18 that contains a previously obtained sample from human (or other animal) breath. Breath collection tube 18 can be any suitable type of tube for collecting and storing a sample obtained from human (or other animal) exhaled breath, including for example those described in U.S. provisional patent application No. 62/896,805 filed 6 Sep. 2019, the entirety of which is incorporated by reference herein.

In the illustrated embodiment, to release substances 2 that have been previously collected and retained in breath collection tube 18 for analysis, breath collection tube 18 is heated, for example to a temperature in the range of about 50° C. to about 300° C. (including any value therebetween, e.g. 75, 100, 125, 150, 175, 200, 225, 250 or 275° C.) to promote the release of such substances from breath collection tube 18.

In some embodiments, including the illustrated example embodiment, to assist in driving substances 2 from breath collection tube 18, gas, which can optionally be heated gas, can be injected from a gas source such as a gas cartridge 19 into breath collection tube 18 and used to collect and drive substances 2 from breath collection tube 18 and be driven into tube 14 of system 10 as inlet flow 13.

FIG. 5 is a side sectional view of a focussing module 70 and example FAIMS cell 40 of system 10A. Cell 40 comprises a pair of parallel plate electrodes 42A, 42B spaced apart by a gap 42C which is typically in the range of about 100 μm to about 600 μm (including any value therebetween, e.g. 125, 150, 175, 200, 225, 250, 275, 300, 325, 350, 375, 400, 450, 500 or 550 μm) to define a transit area 41 therebetween. Cell 40 receives ionized substances 2 which are drawn by vacuum means 50 to flow in a main direction of travel 43 through transit area 41. As depicted in FIG. 1, direction 43 is typically transverse to the gap 42C between electrodes 42A, 42B.

In alternative embodiments, rather than using a FAIMS cell having parallel plate electrodes, other types of FAIMS cells could be used, for example ovoidal, cylindrical, spherical, bullet-shaped, hybrids or combinations thereof, or the like, or any other type of FAIMS cell employing linear and/or radial electric fields.

As depicted in FIG. 1, vacuum means 50 may be located downstream of cell 40. Vacuum means 50 may be configured to draw substances 2 through transit area 41 at a rate which is typically in the range of 0 L/min to 2.0 L/min, including any value therebetween, e.g. 0.1, 0.2, 0.3, 0.4, 0.5, 0.6, 0.7, 0.8, 0.9, 1.0, 1.1, 1.2, 1.3, 1.4, 1.5, 1.6, 1.7, 1.8 or 1.9 L/min. In one example embodiment, vacuum means 50 applies suction at a rate of approximately 1.6 L/min. As described elsewhere herein, vacuum means 50 may be configured to provide suction at a rate which is approximately the same as the rate of introducing flow control gas 6 into system 10.

In some embodiments, flow control valves are provided to adjust the rate of injection of flow control gas 6 and second flow control gas 53 into system 10. For example, if the sum of the flow rate of flow control gases 6 and 53 exceeds the flow rate provided by vacuum means 50, then no atmospheric air injected with the sample will enter FAIMS cell 40, and only ionized substances 2 will enter FAIMS cell 40 due to the electrostatic forces applied by focussing module 70. The respective flow rates of flow control gases 6 and 53 can also be adjusted so that ionized substances 2 experience a net downstream air flow while in FAIMS cell 40, while there is zero net flow or an outward flow out exhaust 25 from ionization chamber 22. In some embodiments, the flow rates of flow control gas 6 and second flow control gas 53 can be matched with the flow rate produced by vacuum means 50 to maintain a desired rate of transit of substances 2 through transit area 41 that is slower than if just flow control gas 6 was used without second flow control gas 53. In some embodiments, flow control gas 6 and flow control gas 53 are pressurized (i.e. supplied at a pressure above atmospheric). In some embodiments, vacuum means 50 can be omitted, so that substances 2 will effectively be pushed through system 10 via the flow of flow control gasses 6 and 53 and/or inlet flow 13.

Each of electrodes 42A, 42B has a surface area facing gap 42C which is typically in the range of about 50 mm$^2$ to about 1,200 mm$^2$ (including any value therebetween, e.g. 75, 100, 200, 300, 400, 500, 600, 700, 800, 900, 1,000 or 1,100 mm$^2$). In some embodiments, electrodes 42A, 42B are rectangular shaped. In these embodiments, each of electrodes 42A, 42B has a length (extending along direction 43) which is typically in the range of 10 mm to 50 mm (including any value therebetween e.g. 15, 20, 25, 30, 35, 40 or 45 mm) and a width (extending in a direction transverse to direction 43 and gap 42C) which is typically in the range of about 5 mm to about 30 mm (including any value therebetween e.g. 10, 15, 20 or 25 mm).

Preferably electrodes 42A, 42B have a thickness which is typically in the range of 5 mm to 15 mm (including e.g. 6, 7, 8, 9, 10, 11, 12, 13 or 14 mm). In some embodiments, first electrode 42A and second electrode 42B have different thicknesses. For example, the thickness of a top electrode 42A may be greater than the thickness of a bottom electrode 42B as depicted in FIG. 5. In some embodiments, the thickness of electrodes 42 is greater than the width of electrodes 42. Thicker electrodes have lower thermal resistance which may advantageously help minimize temperature gradients/differences across their length and width (i.e. thicker electrodes can help maintain a more uniform temperature across transit area 41). In some embodiments, relatively thin electrodes backed by a thermally conductive material such as alumina can be used to provide similar functionality.

Electrodes 42 are made of thermally conductive materials such as stainless steel (e.g. 304 or 316, optionally mirror polished using electrical discharge machining (EDM), nickel, gold, nickel-plated or gold-plated steel, nickel-plated or gold-plated material (e.g. brass, steel or ceramics), metallized ceramics, ceramic PCBs with electroless nickel immersion gold (ENIG) electrodes or gold plated electrodes, and/or gold or nickel coated silica, or the like.

In the example embodiment shown in FIGS. 3-6, electrodes 42A, 42B are partially enclosed by a housing 45. Housing 45 has suitable openings which allow electrodes 42A, 42B to be coupled to suitable voltage sources and/or temperature controllers as described elsewhere herein.

Housing 45 is made from an electrically insulating material to electrically isolate electrodes 42A, 42B from other electrically conductive components of system 10A. In some embodiments, housing 45 is made of suitable FR-4 and/or FR-4/G10 grade materials such as glass-reinforced epoxy laminates, fiberglass composites, etc. In some embodiments, housing 45 is made of ceramic composites such as zirconia based ceramics.

Housing 45 is shaped to provide a cavity 46 (FIG. 9) which receives electrodes 42A, 42B. Where electrodes 42A, 42B are planar electrodes having the shape of a rectangular prism, housing 45 may be shaped to cover up to five faces of each of electrodes 42A, 42B. For example, housing 45 may cover all faces of first electrode 42A except the face facing second electrode 42B and/or all faces of second electrode 42B except the face facing first electrode 42A (i.e. housing 45 may cover all faces of electrodes 42A, 42B except those which define transit area 41).

Figure 8:
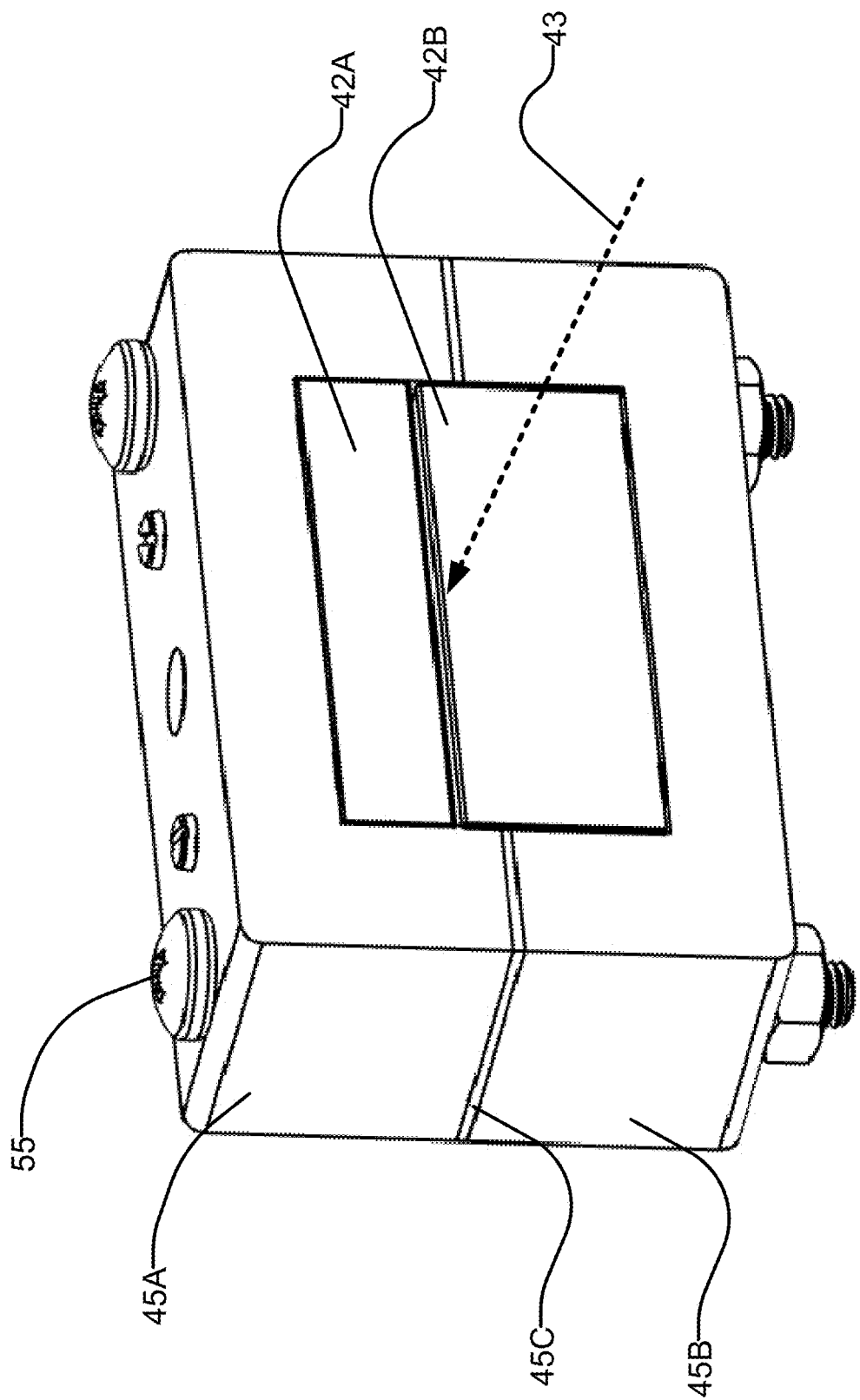
FIG. 8 is a perspective view of a housing enclosing a FAIMS cell of the FIG. 2 system.

In some embodiments, housing 45 comprises a first portion 45A receiving first electrode 42A and a second portion 45B receiving second electrode 42B. First portion 45A and second portion 45B may be coupled through, for example, mechanical fasteners 55 as shown in FIG. 8. In the example embodiment shown in FIG. 8, first and second portions 45A, 45B of housing 45 are U-shaped to cover three faces of each of electrodes 42A, 42B. Housing 45 may optionally comprise one or more gaskets 45C located at an interface between first and second portions 45A, 45B. In some embodiments, gaskets 45C assist in sealing housing 45 around electrodes 42A, 42B.

Figure 9:
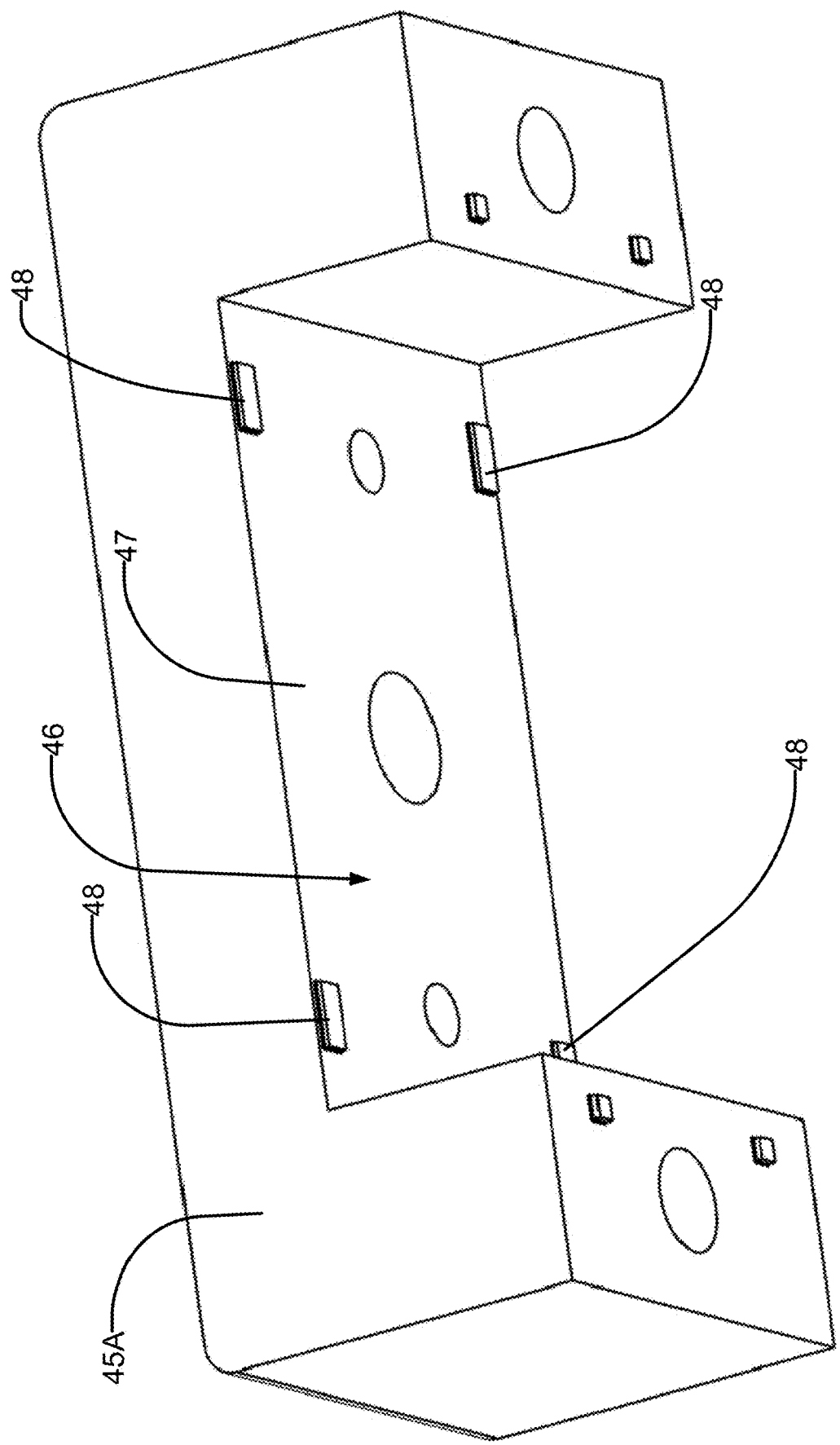
FIG. 9 is a perspective view of part of the FIG. 8 housing.

In some embodiments, housing 45 has an interior surface 47 which is configured to minimize or otherwise reduce contact between housing 45 and electrodes 42A, 42B. For example, housing 45 may comprise footings 48 which are elevated relative to interior surface 47 as depicted in FIG. 9. In the example embodiment shown in FIG. 9, each of first and second portions 45A, 45B of housing 45 comprises four footings 48 that project from interior surface 47 located near the four corners of interior surface 47 of first and second portions 45A, 45B. Footings 48 support electrodes 42A, 42B when they are received in cavity 46, so that the only points of contact between the outer surfaces of electrodes 42A, 42B and interior surface 47 is at footings 48. In some embodiments, the presence of footings 48 assists with manufacturing accuracy, as there are only a few small surfaces of contact with electrodes 42A, 42B, which can be measured and adjusted more efficiently and/or more economically than larger contact surfaces. Footings 48 may have other shapes if desired. Footings 48 may also be provided across a greater portion of the surface area of interior surface 47 than illustrated if desired.

Voltages of different magnitudes and/or periods can be selectively applied to electrodes 42A, 42B to separate a target substance 2A from other substances (e.g. substances 2B, 2C, etc.) as target substance 2A moves through transit area 41. In a currently preferred embodiment, first electrode 42A is driven by a first waveform 44A while second electrode 42B is driven a second waveform 44B (e.g. see FIG. 1). In some embodiments, first waveform 44A and second waveform 44B have the same polarity with respect to ground. In some embodiments, first waveform 44A and second waveform 44B are turned ON during non-overlapping time intervals or during slightly overlapping time intervals. This system is distinct from prior FAIMS systems in which only one electrode is typically driven by a desired waveform and the second electrode remains grounded. Some advantages of driving both electrodes 42A, 42B (instead of only one electrode and keeping the other electrode grounded) include, but are not limited to: increased power efficiency, reduced costs, simplified implementation, and faster switching times. Furthermore, the same waveforms can be used with other types of FAIMS systems, e.g. ovoidal, cylindrical, spherical, bullet-shaped, hybrids or combinations thereof, or the like, or any other type of FAIMS cell employing linear and/or radial electric fields.

Turning first waveform 44A and second waveform 44B ON and OFF controllably (e.g. during non-overlapping time intervals or during slightly overlapping time intervals) can in some cases create a time varying electric field between first electrode 42A and second electrode 42B. Varying the direction of the electric field between first electrode 42A and second electrode 42B over time can cause ionized substances 2 to oscillate between first electrode 42A and second electrode 42B (i.e. oscillate transversely relative to direction 43) as the ionized substances 2 are drawn by vacuum means 50, pushed by the flow of flow control gas 6 and/or pushed by inlet flow 13 to move in main direction 43 through transit area 41.

As an illustrative example, substances 2 may become positively charged after they are ionized by ionization module 20. In this example, the positively charged substances 2 are repelled away from first electrode 42A when first waveform 44A is greater than second waveform 44B (e.g. when first waveform 44A is ON and second waveform 44B is OFF) and repelled away from second electrode 42B when second waveform 44B is greater than first waveform 44A (e.g. when first waveform 44A is OFF and second waveform 44B is ON).

Different substances 2 may accelerate differently and/or have different drift velocities in the presence of an electric field. For example, different substances 2 may have different ionic mobilities and/or different changes to their ionic mobility in the presence of an electric field. The relationship between the ionic mobility of a substance 2 and the magnitude of the electric field is typically non-linear. This can cause different substances 2 to drift toward electrodes 42A, 42B at different velocities when a voltage is applied across first electrode 42A and second electrode 42B. By controllably varying the voltage across electrodes 42A, 42B (e.g. by adjusting first and second waveforms 44A, 44B), a target substance 2A can be separated from other substances (e.g. substances 2B, 2C). For example, a target substance 2A may flow through transit area 41 and out of cell 40 while other substances 2B, 2C collide with one of electrodes 42A, 42B.

Figure 15:
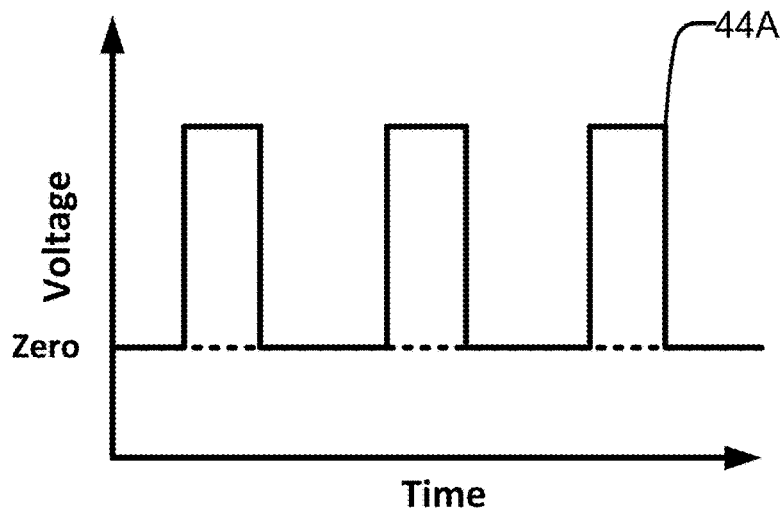
FIG. 15 is a graph of an exemplary waveform driving a first electrode of a FAIMS cell.
Figure 16:
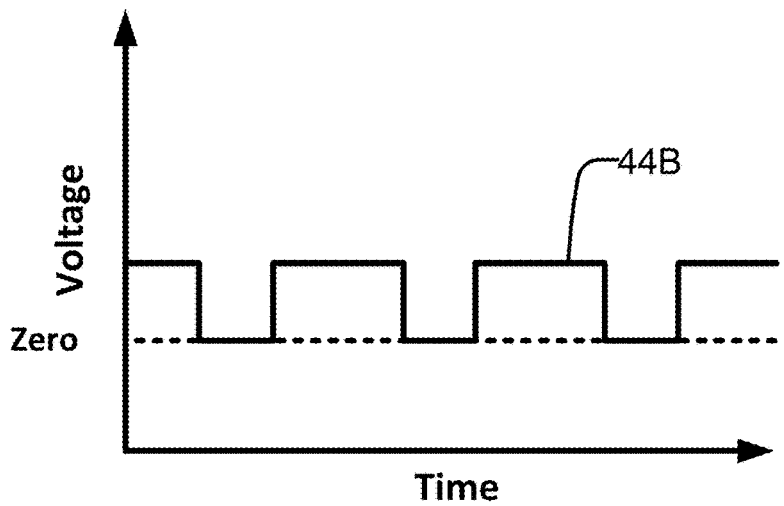
FIG. 16 is a graph of an exemplary waveform driving a second electrode of the FAIMS cell.

FIGS. 15-16 are graphs of exemplary waveforms 44A, 44B applied to electrodes 42A, 42B. In a currently preferred embodiment, waveforms 44A, 44B are square waves or approximations of square waves. In some embodiments, waveforms 44A, 44B are pulse waves.

The term "square wave(s)" described above and elsewhere herein is not limited to ideal square waves. The term "pulse wave(s)" described and elsewhere herein is not limited to ideal pulse waves. It should be understood that square waves and/or pulse waves may have transient overshoot, may be critically damped with round corners, and/or may have rise and/or fall slopes set at certain slew rates (e.g. rise or fall time can sometimes range from about 5 ns to 50 ns) depending on factors such as the size of FAIMS cell 40, the design of switching circuits (e.g. circuits 90, 95), etc. Therefore, square waves and/or pulse waves described herein should be construed in view of their non-ideal characteristics.

In some embodiments, the magnitude of the pulse of either waveform 44A or 44B is greater than the magnitude of the pulse of the other waveform 44B or 44A. In some embodiments, the duty cycle of either waveform 44A or 44B is less than the duty cycle of the other waveform 44B or 44A. In some embodiments, the duty cycle of one of waveforms 44A, 44B is in the range of 15% to 35% and the duty cycle of the other one of waveforms 44A, 44B is in the range of 55% to 85%. In some embodiments, the sum of the duty cycle of waveforms 44A, 44B sums to in the range of about 95% to about 100%. In some embodiments, waveforms 44A, 44B are offset from each other such that only one of waveforms 44A, 44B is active at any given time. In some embodiments, waveforms 44A, 44B are offset from each but slightly overlapping. In some embodiments, the duration of the pulses of the first and second waveforms 44A, 44B are in the range of 200 ns to 2000 ns, including any value therebetween, e.g. 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, or 1950 ns.

In some embodiments, the compensation voltage (CV) value is a virtual CV value that can be calculated by calculating the are under the curve curve on the high side (e.g. 44A) and deducting it from the area under the low side (e.g. 44B). If the difference in area under the curve (Area A=active voltage×time) between 44A and 44B is zero then CV is zero. Anything other than zero produces a "virtual" positive or negative CV. The CV produced by waveforms 44A, 44B may be adjusted to compensate for the drift for a target substance 2A to allow target substances 2A to pass through cell 40, while driving other substances 2B, 2C into electrodes 42A, 42B.

Figure 17:
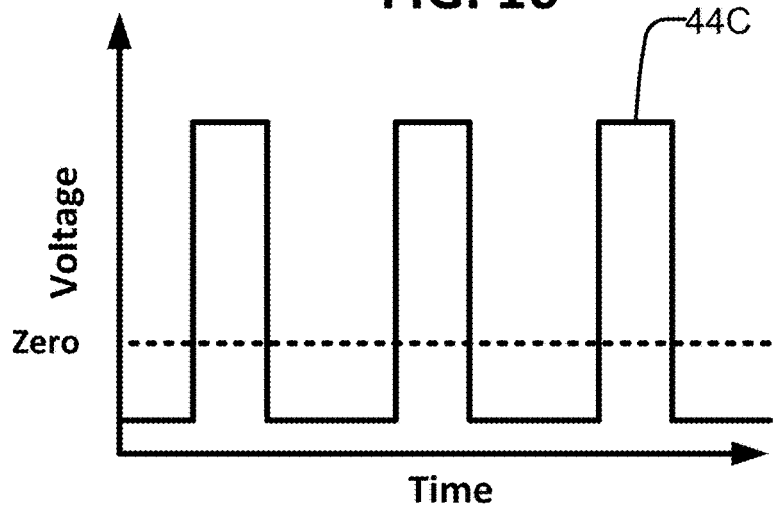
FIG. 17 is a graph of the effective voltage applied across the first and second electrodes as a result of applying the waveforms shown in FIGS. 15 and 16.

Waveforms 44A, 44B have ON voltages which are typically in the range of 500V to 4000V (including any value therebetween, e.g. 600, 700, 800, 900, 1000, 1200, 1400, 1600, 1800, 2000, 2500, 3000 or 3500V). The ON voltages of waveforms 44A, 44B are typically large enough to generate a corresponding electric field between electrodes 42A, 42B which is large enough to non-linearly affect the ionic mobilities of substances 2. First waveform 44A and second waveform 44B typically have different ON voltages and/or different ON durations to apply an asymmetrically shaped effective voltage 44C across electrodes 42A, 42B (e.g. see FIG. 17).

In some embodiments, waveforms 44A, 44B are periodic. In some embodiments, waveforms 44A, 44B have frequencies which are in the range of 500 KHz to 5 MHz (including e.g. 600, 700, 800, 900, 1000, 1100, 1200, 1300, 1400, 1500, 2000, 2500, 3000, 3500, 4000, or 4500 KHz). In some embodiments, the product of the ON voltage and the ON duration of first waveform 44A is the same as the product of the ON voltage and the ON duration of second waveform 44B.

In some embodiments, first waveform 44A and second waveform 44B are generated by the same power source. In some embodiments, first waveform 44A and second waveform 44B are generated by a suitable bridging circuit such as a full bridge circuit or a half bridge circuit.

Figure 18:
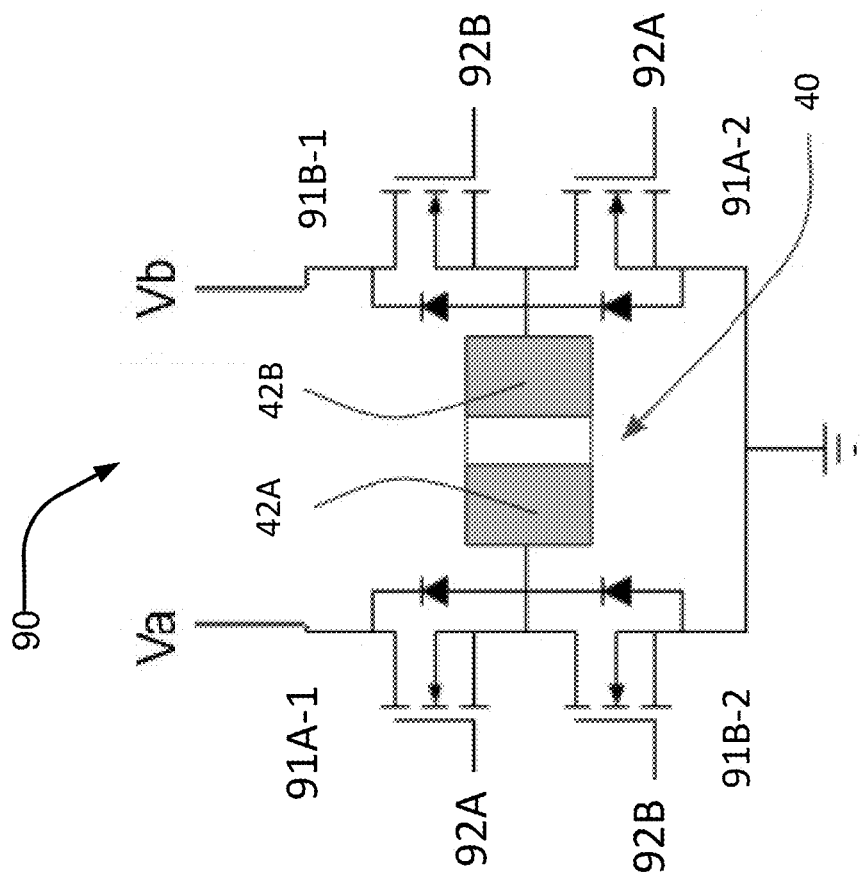
FIG. 18 is a schematic diagram of an exemplary full bridge circuit which may be used to generate the waveforms shown in FIGS. 15-16.

FIG. 18 is a schematic diagram of an exemplary full bridge circuit 90 which may be used to generate waveforms which are suitable for driving cell 40 (e.g. waveforms 44A, 44B). Full bridge circuit 90 comprises electronic switches 91 which can be selectively turned ON and OFF to vary the magnitude, duration and/or polarity of the voltage applied across cell 40.

In the example embodiment shown in FIG. 18, full bridge circuit 90 has a first pair of electronic switches 91A-1, 91A-2 configured to turn ON and OFF at the same time, and a second pair of electronic switches 91B-1, 91B-2 configured to turn ON and OFF at the same time. The first pair of electronic switches 91A-1, 91A-2 and the second pair of electronic switches 91B-1, 91B-2 are typically configured to turn ON at different times (i.e. the first pair of electronic switches 91A-1, 91A-2 and the second pair of electronic switches 91B-1, 91B-2 are turned ON at different time intervals, which may be non-overlapping time intervals in some embodiments, or which may overlap slightly in practice in some embodiments). In some embodiments, the overlap between the time periods that switches 91A-1, 91A-2 and 91B-1 and 91B-2 are turned ON is fine-tuned to optimize the efficiency of the electronics and the overall integrity of the shape of the net signal.

In some embodiments, the first pair of electronic switches 91A-1, 91A-2 is controlled by a first control signal 92A and the second pair of electronic switches 91B-1, 91B-2 is controlled by a second control signal 92B. When the first pair of electronic switches 91A-1, 91A-2 are turned ON by the first control signal 92A, the second pair of electronic switches 91B-1, 91B-2 are turned OFF by the second control signal 92B. Conversely, when the second pair of electronic switches 91B-1, 91B-2 are turned ON by the second control signal 92B, the first pair of electronic switches 91A-1, 91A-2 turned OFF by the first control signal 92A.

In some embodiments, the first pair of electronic switches 91A-1, 91A-2 and the second pair of electronic switches 91B-1, 91B-2 are driven by a single control signal 92. In these embodiments, the first pair of electronic switches 91A-1, 91A-2 may be designed to turn ON when control signal 92 is ON (and OFF when control signal 92 is OFF) while the second pair of electronic switches 91B-1, 91B-2 may be designed to turn ON when control signal 92 is OFF (and OFF when control signal 92 is ON).

In the example embodiment shown in FIG. 18, turning the first pair of electronic switches 91A-1, 91A-2 ON electrically connects the first electrode 42A to a first voltage source Va and the second electrode 42B to ground (creating a first waveform 44A having an ON voltage of Va and an OFF voltage of 0V). Turning the second pair of electronic switches 91B-1, 91B-2 ON electrically connects the second electrode 42B to a second voltage source Vb and the first electrode 42A to ground (creating a second waveform 44B having an ON voltage of Vb and an OFF voltage of 0V). Turning the first pair of electronic switches 91A-1, 91A-2 and the second pair of electronic switches 91B-1, 91B-2 ON and OFF at non-overlapping time intervals or at slightly overlapping time intervals allows full bridge circuit 90 to drive first electrode 42A with first waveform 44A and second electrode 42B with second waveform 44B.

In some embodiments, to produce a virtual compensation voltage (CV) value, Va and Vb can be shifted up and/or down to reach a desired CV. For example with reference to FIG. 18, in one embodiment to increase CV, Va can be increased and/or Vb can be decreased, and to decrease CV, Vb can be increased and/or Va can be decreased.

Figure 19:
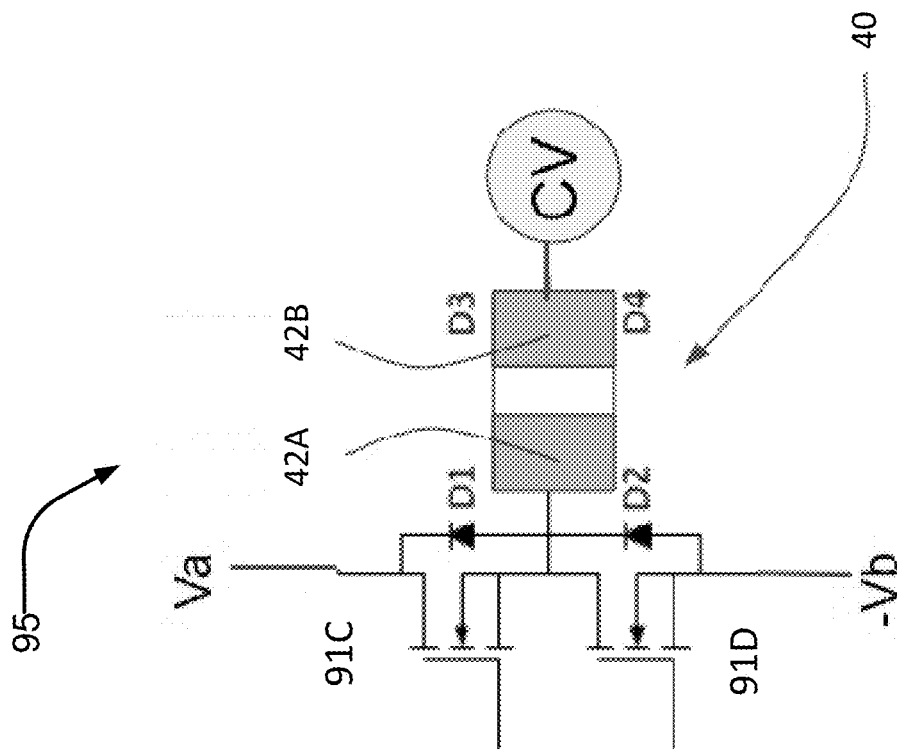
FIG. 19 is a schematic diagram of an exemplary half bridge circuit which may be used to operate the FAIMS cell in the FIG. 2 system.

FIG. 19 is a schematic diagram of an exemplary half bridge circuit 95 which may be used to generate waveforms which are suitable for driving cell 40. Like full bridge circuit 90, half bridge circuit 95 comprises electronic switches 91 which can be selectively turned ON and OFF to vary the magnitude, duration and/or polarity of the voltage applied across cell 40.

In the example embodiment shown in FIG. 19, half bridge circuit 95 comprises first and second electronic switches 91C, 91D configured to turn ON and OFF at different times. First electronic switch 91C is provided between a first voltage source Va and the first electrode 42A. Second electronic switch 91D is provided between a second voltage source Vb and the first electrode 42A. A third voltage source CV is connected to the second electrode 42B.

In the example embodiment shown in FIG. 19, first voltage source Va provides a voltage with is greater than the voltage provided by third voltage source CV and third voltage source CV provides a voltage which is greater than second voltage source Vb. Turning first electronic switch 91C ON electrically connects the first electrode 42A to the first voltage source Va to apply a positive voltage across cell 40 (i.e. the voltage at first electrode 42A is greater than the voltage at second electrode 42B). On the other hand, turning second electronic switch 91D ON electrically connects the first electrode 42A to the second voltage source Vb to apply a negative voltage across cell 40 (i.e. the voltage at first electrode 42A is smaller than the voltage at second electrode 42B). Turning the first and second electronic switches 91C, 91D ON and OFF at non-overlapping or slightly overlapping time intervals allows half bridge circuit 95 to drive cell 40 with an asymmetric waveform.

In some embodiments, electronic switches 91 comprise transistors such as metal-oxide-semiconductor field-effect transistors (MOSFETs), SiC MOSFETs, or the like. Electronic switches 91 may comprise n-type transistors, p-type transistors, or a combination of both n-type and p-type transistors. Electronic switches 91 may comprise other types of microelectronic devices such as solid state relays, microelectromechanical relays, etc.

In some embodiments, electrodes 42A, 42B are thermally coupled to one or more temperature controllers 46. Each of electrodes 42A, 42B may be coupled to a respective temperature controller 46A, 46B. Each of temperature controllers 46A, 46B may be independently controlled.

In the example embodiment shown in FIGS. 3-6, electrodes 42A, 42B are coupled to their respective temperature controllers 46A, 46B through thermally conductive rods 49A, 49B. Rods 49 are made of thermally conductive materials such as alumina or the like. Rods 49 are preferably either made of an electrically isolating material or shielded with an electrical isolation barrier (e.g. Kapton/Polyamide tape, PTFE, glass bushing, etc.). In a currently preferred embodiment, rods 49 are in direct physical contact with electrodes 42 to transfer heat toward or away from electrodes 42 through conduction. For example, rods 49 may be heated by temperature controller 46 to thereby heat electrodes 42. Alternatively, rods 49 may be cooled by temperature controller 46 to thereby cool electrodes 42. Rod 49 may be provided through an opening of housing 45 to physically contact electrode 42.

In some embodiments, electrodes 42 and/or housing 45 are in thermal contact with a heating and/or cooling jacket, a plurality of thermally wires (e.g. nickel-chromium wires) distributed over one or more surfaces thereof that can act as a heating element e.g. by converting electric current to heat, or the like, to assist with controlling the temperature of electrodes 42.

Figure 10:
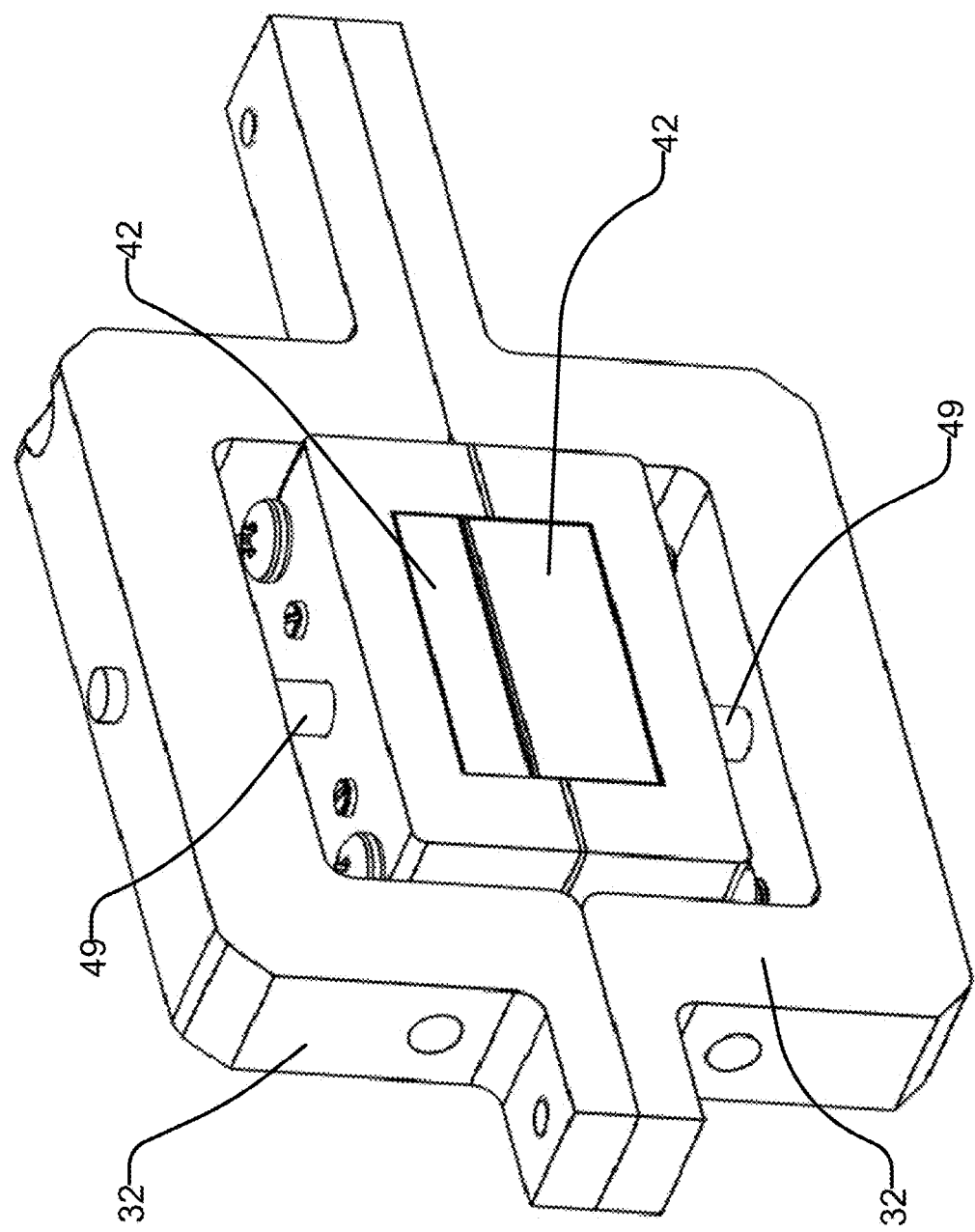
FIG. 10 is a perspective view of an example embodiment of a FAIMS cell having a heating bracket.

For example, in the example embodiment illustrated in FIG. 10, a heating bracket 32 is provided that is in contact with thermally conductive rods 49 so that heating bracket 32 can be used to heat electrodes 42.

Figure 11:
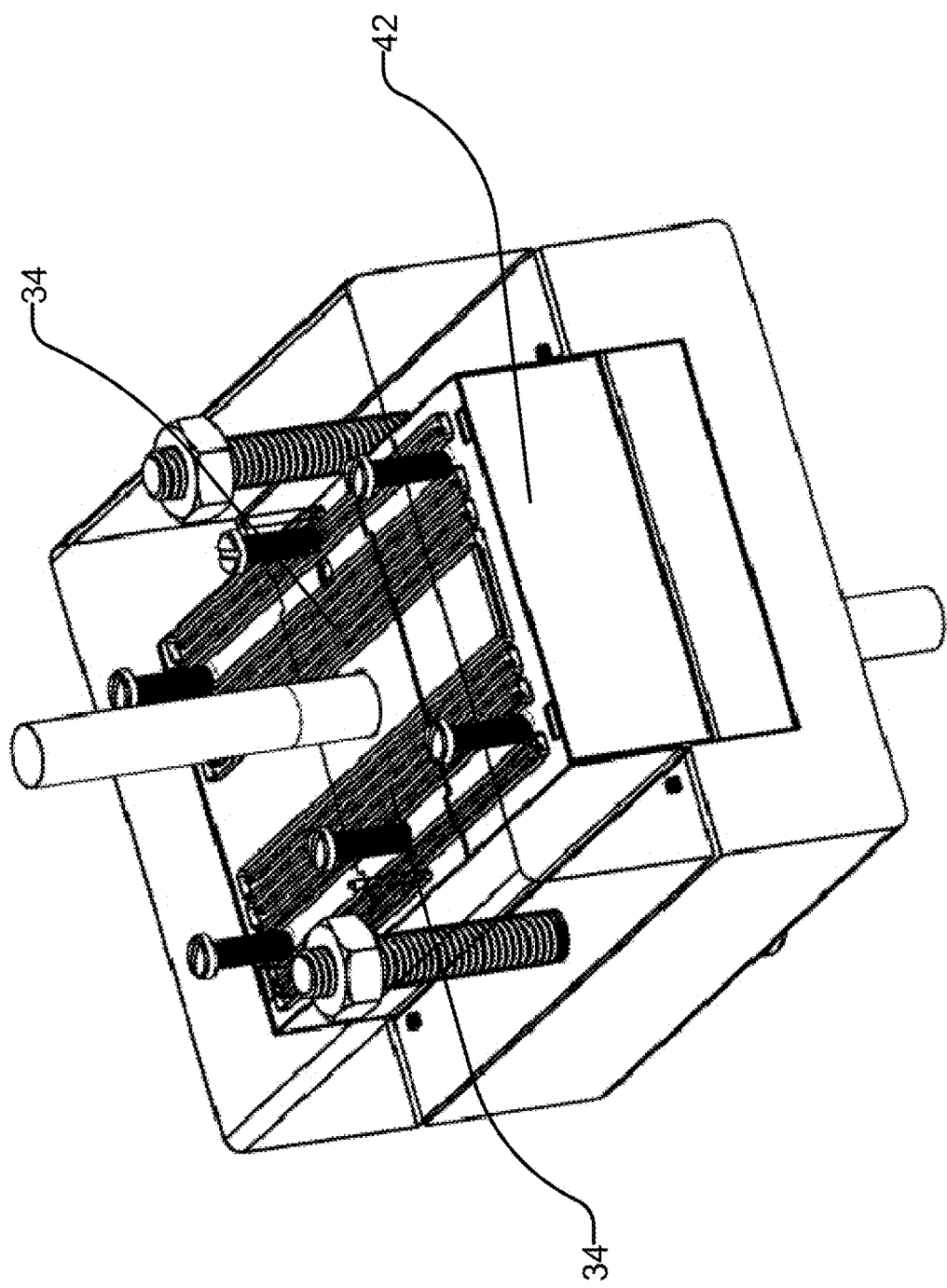
FIG. 11 is a perspective view of an example embodiment of a FAIMS cell provided with a plurality of fine wires for heating the electrodes thereof.

In the example embodiment illustrated in FIG. 11, a plurality of thermally conductive wires 34 are provided on a surface of electrodes 42, so that thermally conductive wires 34 can be coupled to a suitable heat source, and/or an electric current can be passed through such thermally conductive wires 34 to generate heat, and used to supply heat to electrodes 42. In such embodiments, it is not necessary to provide thermally conductive rods 49. In such embodiments, a temperature sensor can be optionally provided in place of the thermally conductive rods 49 to monitor the temperature of electrode 42 and/or dynamically control the temperature of the electrode 42 (e.g. via a controller). This configuration can in some cases control the temperature of electrodes 42 very precisely since the electrodes 42 are heated via the wires 34 and monitored via an independent temperature sensor.

Figure 12:
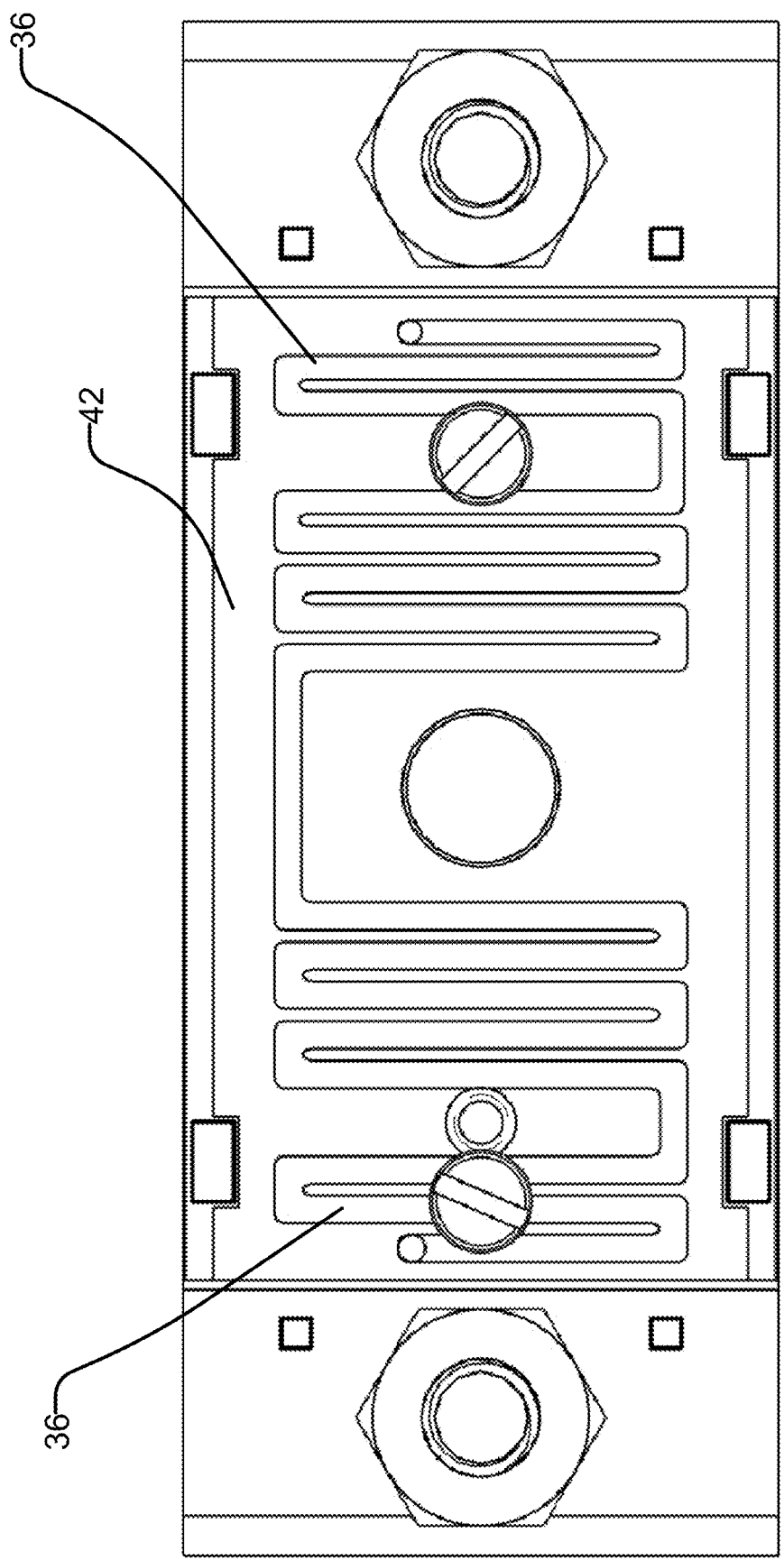
FIG. 12 is a top view of an example embodiment of a FAIMS cell provided with a fluid flow path in thermal contact with the electrodes thereof that can be used to supply a fluid for heating and/or cooling the electrodes.

In the example embodiment illustrated in FIG. 12, a fluid flow path 36 is provided in thermal contact with electrodes 42. A suitable fluid, e.g. water or coolant, can be passed through fluid flow path 36, and either heated or cooled (depending on whether it is desired to heat or cool electrodes 42) to heat or cool, respectively, electrodes 42.

In some embodiments, electrodes 42 are maintained at a constant temperature as substances 2 are drawn by vacuum means 50 to move in main direction 43 through transit area 41. For example, electrodes 42 may be maintained at a temperature which is in the range of 50° C. to 250° C. (including e.g. 60, 70, 80, 90, 100, 110, 120, 130, 140, 150, 175, 200 or 225° C.). In some embodiments, electrodes 42 are maintained at a temperature in the range of 70° C. to 200° C. In some embodiments, controlling the temperature of electrodes 42 involves cooling electrodes 42 (e.g. via conduction through rods 49) as they are driven by waveforms 44. Since a change in the temperature gradient across electrodes 42 will result in a change in the electric field as the electric field is temperature dependent, maintaining electrodes 42 at a constant temperature, particularly along the length of main direction 43, can advantageously improve the resolving power of cell 40 by reducing noise caused by temperature fluctuations. In some embodiments, substantially all of the surface area of electrodes 42 facing transit area 41 is maintained at a consistent temperature. In some embodiments, substantially all of the volume of transit area 41 is maintained at a constant temperature, to avoid the formation of a temperature gradient between electrodes 42A, 42B.

In some embodiments, temperature controllers 46 comprise one or more temperature sensors (not shown) which can monitor the temperature of electrodes 42 and/or transit area 41. For example, one or more temperature sensors may be provided as part of rod 49 and/or may be provided in contact with one or more points on electrode 42. Temperature controllers 46 may adjust the temperature of electrodes 42 based on the readings of the temperature sensors.

An issue with use of a FAIMS cell such as FAIMS cell 40 is that a repellent electrical field is generated by the FAIMS cell 40 that can repel ions as they approach the FAIMS cell 40. Additionally, fringe fields can be created at the entrance and exit to/from the FAIMS cell due to the corners of the electrodes. In some embodiments, system 10 comprises a focussing module 70 provided to help guide and/or push the ionized substances 2 into transit area 41 of cell 40. In the illustrated embodiment, focussing module 70 uses ion optics to focus the ionized substances 2, and focussing module 70 has one or more focussing electrodes 72 driven by voltages which are typically in the range of about 50V to about 1000V, including any value therebetween e.g. 75, 100, 150, 200, 250, 200, 350, 400, 500, 600, 700, 800 or 900V. Each of the focussing electrodes 72 may be driven at a different offset voltage to create a voltage gradient between the focussing electrodes 72. Each of the focussing electrodes 72 may be driven at a predetermined voltage.

Focussing electrodes 72 are shaped to generate radial electric fields when they are charged to guide or otherwise steer ionized substances 2 along a path which is preferably parallel to direction 43 before they enter cell 40. Guiding ionized substances 2 in this manner allows ionized substances 2 to enter cell 40 at an angle which is generally perpendicular to gap 42C. Guiding ionized substances 2 in this manner can in some cases allow ionized substances 2 to enter cell 40 at a generally constant angle (e.g. preferably straight on and parallel to direction 43). This can advantageously improve the resolving power of cell 40 by reducing noise caused by introducing substances 2 into cell 40 at different angles.

In some embodiments focussing electrodes 72 are axially symmetric about a central axis 73 which is parallel to direction 43 and/or parallel to a central axis of tube 14. For example, focussing electrodes 72 may be ring-shaped electrodes, round plates, or conically-shaped electrodes (e.g. ring-shaped or round plate electrodes which are conical rather than flat to radially guide ions towards a central axis). Focussing electrodes 72 do not necessarily need to be round or ring or conical electrodes, but they should be positioned, shaped and/or configured to apply a radial component of electromagnetic force on ion substances 2 moving through focussing module 70, as well optionally an axial component of electromagnetic force to move ionized substances 2 from ionization chamber 22 through focussing module 70 and into FAIMS cell 40.

Figure 20:
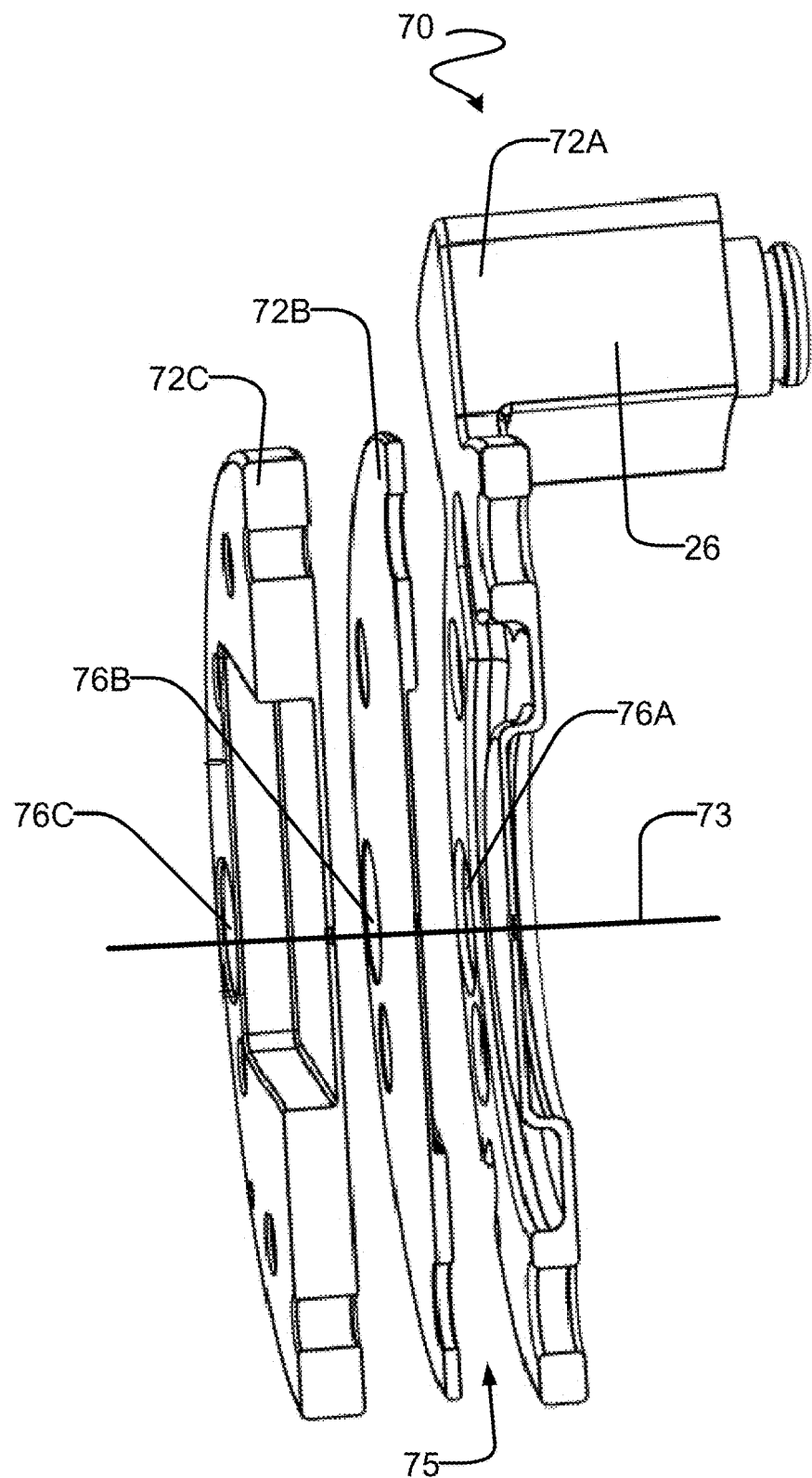
FIG. 20 is an exploded view of a focussing module according to an example embodiment.

FIG. 20 is an exploded view of an exemplary focussing module 70 of system 10A. Focussing module 70 comprises three axially spaced apart electrodes 72A, 72B, 72C, each of which is axially symmetric around a common central axis 73. In the FIG. 20 example embodiment, first electrode 72A is the electrode 72 which is closest to ionization module 20 and furthest away from cell 40, and third electrode 72C is the electrode 72 which is furthest from ionization module 20 and closest to cell 40.

Each of the axially spaced apart electrodes 72A, 72B, 72C may be driven at different voltages to create a voltage gradient between electrodes 72. In some embodiments, first electrode 72A is driven at a voltage which is greater than second electrode 72B, and second electrode 72B is driven at a voltage which is greater than third electrode 72C. For example, first electrode 72A may be driven at a voltage which is typically in the range of about 500 to about 700 V, second electrode 72B may be driven at a voltage which is typically in the range of about 300 to about 500 V, and third electrode 72C may be driven at a voltage which is typically in the range of about 100 to about 300 V. Electrodes 72A, 72B, 72C may be driven at any suitable voltage, and in alternative embodiments, third electrode 72C could be driven at a higher voltage than second electrode 72B and/or first electrode 72A, and likewise second electrode 72B could be driven at a higher voltage than first electrode 72A.

Electrodes 72 have a thickness (in the axial direction) which is typically in the range of about 0.3 mm to about 3.0 mm (including e.g. 0.4, 0.5, 0.6, 0.7, 0.8, 0.9, 1.0, 1.2, 1.4, 1.6, 1.8, 2.0, 2.2, 2.4, 2.6 or 2.8 mm). The thickness of each of the electrodes 72 may be different from each other in some cases. In some embodiments, the thickness of first electrode 72A is greater than the thickness of second electrode 72B and the thickness of second electrode 72B is greater than the thickness of third electrode 72C.

Electrodes 72 are spaced apart from each other in the axial direction. First electrode 72A and second electrode 72B may be spaced apart by a distance which is typically in the range of about 0.4 mm to about 5 mm (including e.g. 0.5, 0.6, 0.7, 0.8, 0.9, 1.0, 1.2, 1.4, 1.6, 1.8, 2.0, 2.5, 3.0, 3.5, 4.0 or 4.5 mm), and second electrode 72B and third electrode 72C may be spaced apart by a distance which is typically in the range of about 0.4 mm to about 2 mm (including e.g. 0.5, 0.6, 0.7, 0.8, 0.9, 1.0, 1.2, 1.4, 1.6 or 1.8 mm). The spacing between first electrode 72A and second electrode 72B may be different from the spacing between second electrode 72B and third electrode 72C in some cases. In some embodiments, the spacing between first electrode 72A and second electrode 72B is greater than the spacing between second electrode 72B and third electrode 72C.

Each of electrodes 72 is typically mounted on or otherwise supported by or formed as a corresponding plate 74. Each of plates 74 comprises a corresponding aperture 76 located along central axis 73. Apertures 76 may be circular shaped. Aperture 76 may have diameters which are typically in the range of about 0.4 mm to about 5 mm (including e.g. 0.5, 0.6, 0.7, 0.8, 0.9, 1.0, 1.2, 1.4, 1.6, 1.8, 2.0, 2.5, 3.0, 3.5, 4.0 or 4.5 mm). The size of apertures 76 of each of the plates 74 may be different in some cases. In some embodiments, the size of the aperture 76A of first plate 74A is greater than the size of the aperture 76B of the second plate 74B, and the size of the aperture 76B of second plate 76B is greater than the size of the aperture 76C of the third plate 76C.

Although focussing module 70 has been illustrated as having three focussing electrodes 72A, 72B and 72C, in alternative embodiments, different numbers of focussing electrodes could be used, e.g. 2, 4 or 5. Higher numbers of focussing electrodes may increase the path length that substances 2 must travel to pass through focussing module 70, and/or may present additional opportunities for substances 2 to collide with the electrodes (and therefore not be passed to FAIMS module 40 for subsequent detection). A balancing of such factors with the increased focussing that might be provided by the use of additional focussing electrodes will need to be made in each case.

In alternative embodiments, other structures could be used as focussing module 70 to provide the ion optics used to focus ionized substances 2 for entry into FAIMS cell 40. In further alternative embodiments, focussing module 70 could use other principles of operation to focus ionized substances 2 for entry into FAIMS cell 40, for example, a magnetic lens could be used.

In some embodiments, alternative focussing techniques could be used to focus ionized substances 2 for entry into FAIMS cell 40. For example, in one example embodiment if focussing electrodes 72A, 72B and 72C are operated out of phase but at the same voltage, it can be possible to trap ionized substances within focussing module 70 and then subsequently push the accumulated ionized substances 20 into cell 40 using electrostatics. In some embodiments, pneumatic and/or aerodynamic forces may be used to provide assistance for focussing and/or directing ionized substances 2 for entry into FAIMS cell 40.

As described elsewhere herein, focussing module 70 may comprise a means for introducing a flow control gas 6 into system 10A. For example, focussing module 70 may comprise one or more inlet ports 26 which introduce flow control gas 6 into system 10A at the space 75 located between first electrode 72A and second electrode 72B as depicted in FIG.

Figure 21:
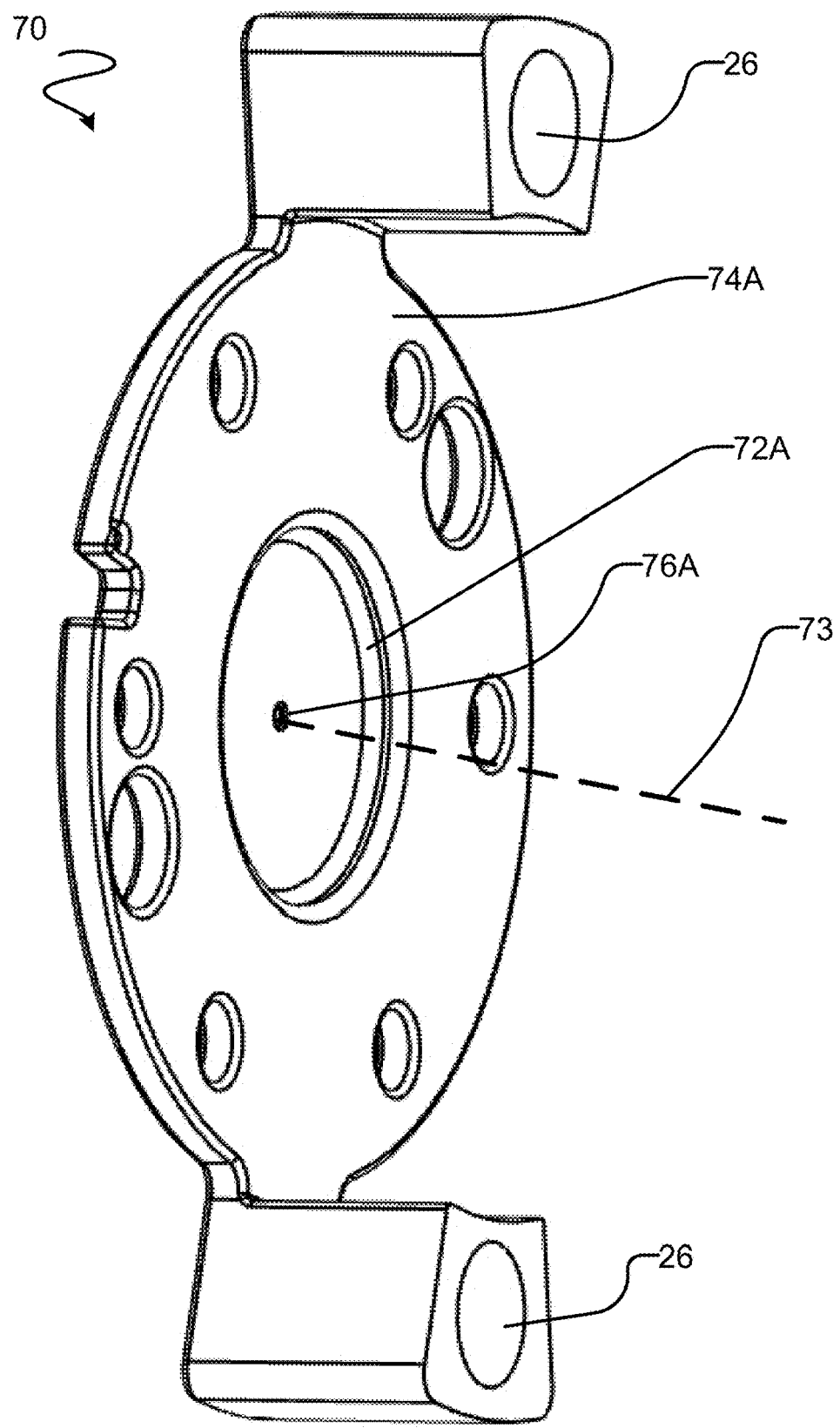
FIG. 21 is a perspective view of a focussing electrode which forms part of the FIG. 20 focussing module.

20. In the example embodiment shown in FIG. 20, inlet ports 26 are positioned to allow flow control gas 6 to flow radially inward towards central axis 73 until it is drawn through second aperture 76B by vacuum means 50. FIG. 21 is a view of just first electrode 72A showing more clearly aperture 76A formed therein.

Figure 22:
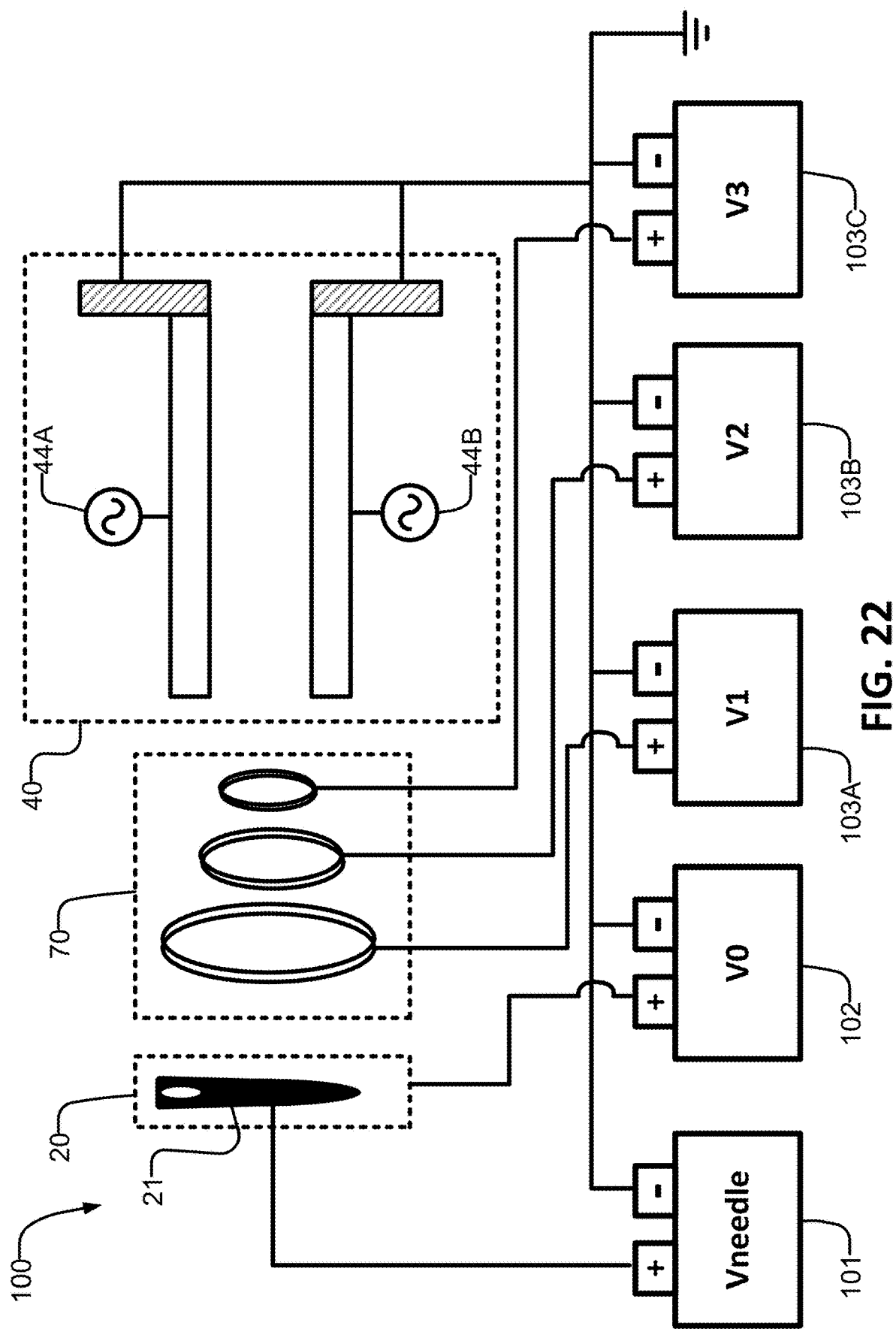
FIG. 22 is a schematic diagram of a circuit which may be used to operate the focussing module shown in FIGS. 20-21.

FIG. 22 is a schematic diagram of a circuit 100 which may be used to operate ionization module 20 and/or focussing module 70. Circuit 100 comprises a plurality of power supplies which can be configured to produce a desired voltage. In some embodiments, circuit 100 comprises an ionization power supply 101 configured to produce and provide a voltage which is typically in the range of 2,500V to 3,000V to the needles 21 of ionization module 20. In some embodiments, circuit 100 comprises a biasing power supply 102 configured to produce and deliver a biasing voltage which is typically in the range of 2,500V to 3,000V to bias ionization chamber 22 of ionization module 20.

In some embodiments, circuit 100 comprises a separate power supply 103 for each electrode 72. In other embodiments, circuit 100 comprises a smaller number of power supplies 103 compared to the number of electrodes 72. For example, circuit 100 may comprise a single power supply 103 and suitable regulating circuits and/or potentiometers to deliver different voltages to electrodes 72.

In some embodiments, power supplies 101, 102, 103 are coupled to one or more boost DC-DC converter circuits to produce a desired voltage. In alternative embodiments, other suitable types of circuitry can be used.

Generally speaking, in certain embodiments, an improved apparatus for conducting FAIMS analysis is provided. In one example embodiment illustrated schematically in FIG. 23, an example embodiment of a system 210 for detecting target substances 202A from a plurality of input substances 202 is provided. System 210 defines a flow path that has an inlet 212 into which an inlet flow 213 containing a plurality of substances 202 is provided. Inlet flow 213 is directed towards an ionization module 220, which may be any suitable type of ionization module including those described herein, e.g. one or more corona discharge needles, electrospray ionization, radioactive ionization, photoionization, desorption ionization (e.g. laser), dielectric barrier discharge (DBD), suitable ionization filaments and the like.

Input substances 202 are a mixture of target substances 202A and other non-target substances such as substances 202B and 202C (not shown) from which it is desired to separate target substances 202A. As used in FIG. 23, 202' refers to a combination of substances 202A, 202B and 202C that have been ionized as discussed below. Input substances 202 may also include some substances 202D that are undesired, for example because they cannot be ionized or may interfere with the ionization of substances 202'. An example of such an undesired substance 202D is water, for example as may be supplied via breath or via a previously collected breath sample.

In some embodiments, including the illustrated embodiment, system 210 supplies a flow control gas 206 via an inlet port positioned upstream of a FAIMS cell 240 that can be used to regulate the flow of inlet flow 213 and substances 202. In the illustrated embodiment, the inlet for supplying flow control gas 206 is positioned downstream of and in the vicinity of ionization module 220. In some other embodiments, the inlet for supplying flow control gas 206 is provided within focussing module 270.

To regulate the flow of inlet flow 213 and substances 202, flow control gas 206 can be supplied at a rate such that there is a limited degree of downstream fluid flow in the vicinity of ionization module 220 or even a slightly upstream level of fluid flow in the vicinity of ionization module 220, so that unionized substances 202D, which may include water, are forced out of outlet 225, as shown by the arrow labelled 202D, rather than being allowed to remain in the vicinity of ionization module 220 or to enter focussing module 270 or FAIMS cell 240.

As an example of how the flow control gas 206 can be used to regulate the movement of substances 202 within the fluid flow path that is defined within system 210, in some embodiments such as the embodiment illustrated in FIG. 24, system 210 has a vacuum source 250 that is used to cause a downstream fluid flow by providing suction at the downstream end of the fluid flow path defined within system 210. This causes a downstream fluid flow, which could be on the order of about 0 L/minute to 2.0 L/minute in some exemplary embodiments as described above. The introduction of flow control gas 206 upstream of FAIMS cell 240 will cause a localized change in the rate of fluid flow, particularly if the flow rate of the combination of inlet flow 213 and flow control gas 206 is different from the downstream fluid flow generated by vacuum source 250. Likewise, in embodiments without vacuum source 250 (such as the embodiment of FIG. 23), the rate of fluid flow within system 210 will be determined by the respective flow rates of inlet flow 213 and flow control gas 206.

Thus, by supplying flow control gas 206 upstream of FAIMS cell 240 at a rate approaching or greater than the rate of suction applied by vacuum source 250, a small downstream or even net upstream flow that can exit system 210 via outlet 225 can be generated. The net upstream flow means that unionized substances 202D will be carried by the net fluid flow out of outlet 225.

In contrast, ionized substances 202' can be guided using a combination of electrostatic forces provided by focussing module 270 (e.g. via suitable ion optics), optionally together with the fluid flow caused by the combination of inlet flow 213 and flow control gas flow 206, to enter focussing module 270 and subsequently FAIMS cell 240. In some embodiments, focussing module 270 is any type of focussing module described herein, e.g. one or a plurality of focussing electrodes capable of exerting a radial component of electromagnetic force, a magnetic lens, apparatus for exerting pneumatic and/or aerodynamic focussing forces, or the like, or any other apparatus suitable to achieve the desired focusing effect on ionized substances 202'.

From focussing module 270, ionized substances 202' can enter FAIMS cell 240, which can be any suitable type of FAIMS cell, e.g. ovoidal, cylindrical, spherical, bullet-shaped, hybrids or combinations thereof, or the like, or any other type of FAIMS cell employing linear and/or radial electric fields. From FAIMS cell 240, the substances 202A that have passed through the FAIMS cell 240 can then be passed to a suitable detector or analyzer 260 to detect and/or analyze the desired substances 202A that have been passed through FAIMS cell 240, for example a Faraday cup detector, single plate detector, metal oxide sensor, chemical detector including a chemical reaction, conformational change in a detecting substance and/or chemical adsorption triggered by or sensitive to the substance of interest, mass spectrometer, or the like.

In some embodiments, as illustrated in FIG. 24, a second inlet can be provided for introducing a further portion of the flow control gas 253 downstream of FAIMS cell 240. This can allow for further control of the rate of flow of substances 202' through FAIMS cell 240, for example by decreasing the rate of fluid flow through FAIMS cell 240 so that substances 202' will experience a longer residence time within FAIMS cell 240.

Apparatus such as system 210 may be used to detect any type of molecules that can be detected using conventional mass spectrometry techniques. Without being bound by theory, apparatus such as system 210 may be particularly useful in detecting non-volatile substances from breath. Examples of non-volatile substances that may be found in breath include illicit substances such as Δ-9-tetrahydrocannabinol and various metabolites thereof, as well as other illicit substances such as fentanyl, as well as other substances such as nicotine and caffeine. Unlike alcohol and other highly volatile substances that can be easily detected in breath, it is difficult to detect such non-volatile substances in breath, meaning more invasive collection methods such as collecting a urine sample or a blood sample must be used. While FAIMS can detect non-volatile substances in laboratory settings, obtaining a sufficient amount of such non-volatile substances from a biological sample has proven to be a challenge. The presence of high levels of moisture that accompany a sufficient amount of such non-volatile substances for detection complicates e.g. the ionization step of FAIMS. Thus, apparatus such as system 210 which allow for the ionization and focusing of substances while facilitating removal of undesired substances such as water may have particular application in detecting non-volatile substances from breath. Such technology is also potentially applicable to the detection of larger macromolecules, for example specific proteins or nucleic acid fragments, from breath, to enable potential detection of biological disorders or pathogens from a breath sample.

A wide range of variations are possible within the scope of the present invention. These variations may be applied to all of the embodiments described above, as suited, and include, without limitation:

- system 10 may be configured to separate substances 2 into any number of separated substances 2A, 2B, 2C . . . 2N and detector 60 may be configured to detect any number of substances 2A, 2B, 2C . . . 2N.
- system 10 may be configured to separate and/or detect substances 2 of different sizes (e.g. heavier substances having a higher molecular weight such as biological macromolecules may require system 10 to be configured differently compared to the configurations used for small molecules).
- detector 60 may comprise any suitable detectors, examples of which include but are not limited to conductive plates, metal oxide sensors, Faraday cups/cages, etc.
- detector 60 may comprise or be substituted with additional analytical instruments such as a mass spectrometer, an additional system like system 10A, etc.
- suitable ion optics may be provided between cell 40 and detector 60 to further improve the resolving power of system 10.
- cell 40 may comprise electrodes of any suitable geometry (i.e. cell 40 does not necessarily need to have parallel plate electrodes). For example, cell 40 may comprise ovoidal shaped electrodes, cylindrical electrodes, bullet shaped electrodes, etc.
- focussing module 70 may comprise any suitable components and/or arrangement of components operative to guide ionized substances 2 into cell 40 in a desirable manner. Focussing module 70 may provide other types of forces (e.g. magnetic forces) in addition or in alternative to electrostatic forces to guide ionized substances 2 into cell 40 in a desirable manner.
- although the operation of system 10 has been described with reference to operation in an ambient atmosphere, any desired environment could be used depending on the desired application, for example the system could operate in an inert gas environment, for example nitrogen or argon.
- although focussing module 70 has been described as being deployed upstream of FAIMS cell 40, a similar ion optics module could be deployed downstream of FAIMS cell 40 to assist in focusing separated ionized substances 2 into detector 60.
- alternative focussing and/or filtering modules can be used upstream or downstream of the components described herein to further assist in enhancing the signal-to-noise ratio that can be achieved by system 10.

EXAMPLES

Further aspects of the invention are further described with reference to the following examples, which are intended to be illustrative and not limiting in scope.

Example 1.0—Experimental Analysis of FAIMS Cell for Detection of THC

Experiments were conducted by the inventors using systems of a type as described for system 10. The experiments were conducted to detect THC in the presence of nicotine. THC is highly hydrophobic and has low volatility, and does not readily enter the gas phase. Nicotine was selected as a secondary analyte for the experiment because it is partially hydrophobic, and is, like THC, in the intermediate mass range, and is expected to be commonly encountered in the field.

While it has its own detector for portable field operations, the system used in the experiment is also designed to interface directly with a mass spectrometer for calibration and validation of results. During these experiments, the system was coupled with a triple quadrupole mass spectrometer (e.g. a Thermo™ TSQ) set to positive ion mode. This instrument allows for additional validation of peak identification by MS/MS.

Samples were passed through atmospheric pressure chemical ionization (APCI) needles and were ionized. The novel APCI configuration was found to effectively ionize THC. It was found that the ionization energy (voltage applied to the needles) determines the type of THC ion that is observed. Mass spectra show predominantly the $[M+H]^+$ ion (m/z 315) unless the ionization energy is set to a higher value (>4 kV), at which the THC molecule begins to deprotonate and recombine to form a different ion at m/z 313.

Ions are focused and directed into the FAIMS cell by a system of electrostatic lenses (in the nature of focusing module 70 described above), which were found to increase ion transmission by 2-4× and improve signal/noise ratio. Aerodynamic and electrostatic forces are balanced in order to achieve the number of ion oscillations needed to resolve the different analytes.

Particular analyte ions of interest are selected by setting their appropriate compensation voltage (CV) values. These ions are then allowed to transmit through and exit the FAIMS cell. If the device is in the field, an onboard detector can be used. If the device is being calibrated, as in these experiments, then analyte ions will bypass the device detector and enter a mass spectrometer, in which the ions are identified and validated, and further analyses can also be conducted, if needed.

The FAIMS device was calibrated using standards diluted in methanol. Two drops of 1 ppm nicotine and 3 drops of 1 ppm THC were added to the device sample collection region. The compensation voltage was scanned to determine the value corresponding to the highest intensity peak for each respective analyte. This compensation voltage value was then fixed to enable field detection of that analyte.

Figure 25:
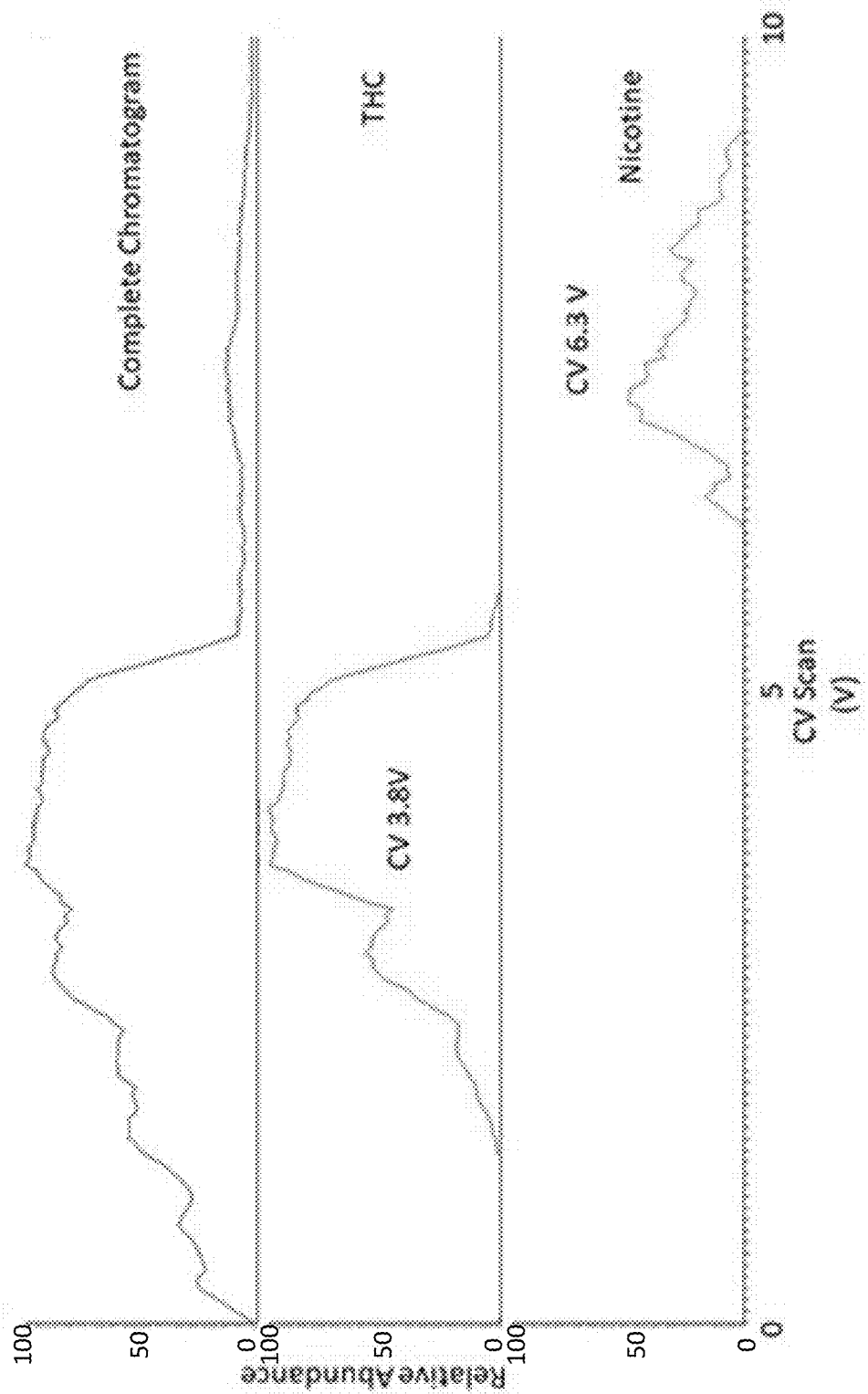
FIG. 25 shows compensation voltage (CV) chromatograms of the complete signal (top), signal for THC (center), and signal for nicotine (bottom) in an experiment conducted by the inventors.

For these experiments, the compensation voltage was scanned from 0 to 10 V. FIG. 25 shows the ion signal intensity for the total chromatogram, which refers to all ions that transmit and reach the detector, and individual chromatograms for each respective analyte (THC signal shown in the middle panel, nicotine in the bottom panel). THC and nicotine are fully resolved from each other, as their compensation voltage peaks do not overlap. The peak compensation values for each analyte were also distinct; THC is 3.8V, and nicotine is 6.3V. This scan was repeated ten times to ensure reproducibility of the compensation voltage values.

Example 2.0—Evaluation of Samples Obtained from Breath

In a breath testing exercise, test subjects were asked to concurrently consume cannabis (½ marijuana cigarette, containing approximately 25 mg of THC) and nicotine (½ cigar, containing approximately 50 mg of nicotine).

Breath samples were taken with a breath capture unit (BCU), which provides an accurate volume and flow rate of breath, among other parameters. Five to seven breaths, or a volume of 4 L, were collected and immediately analyzed onsite with the FAIMS device. No sample preparation is required.

Figure 26:
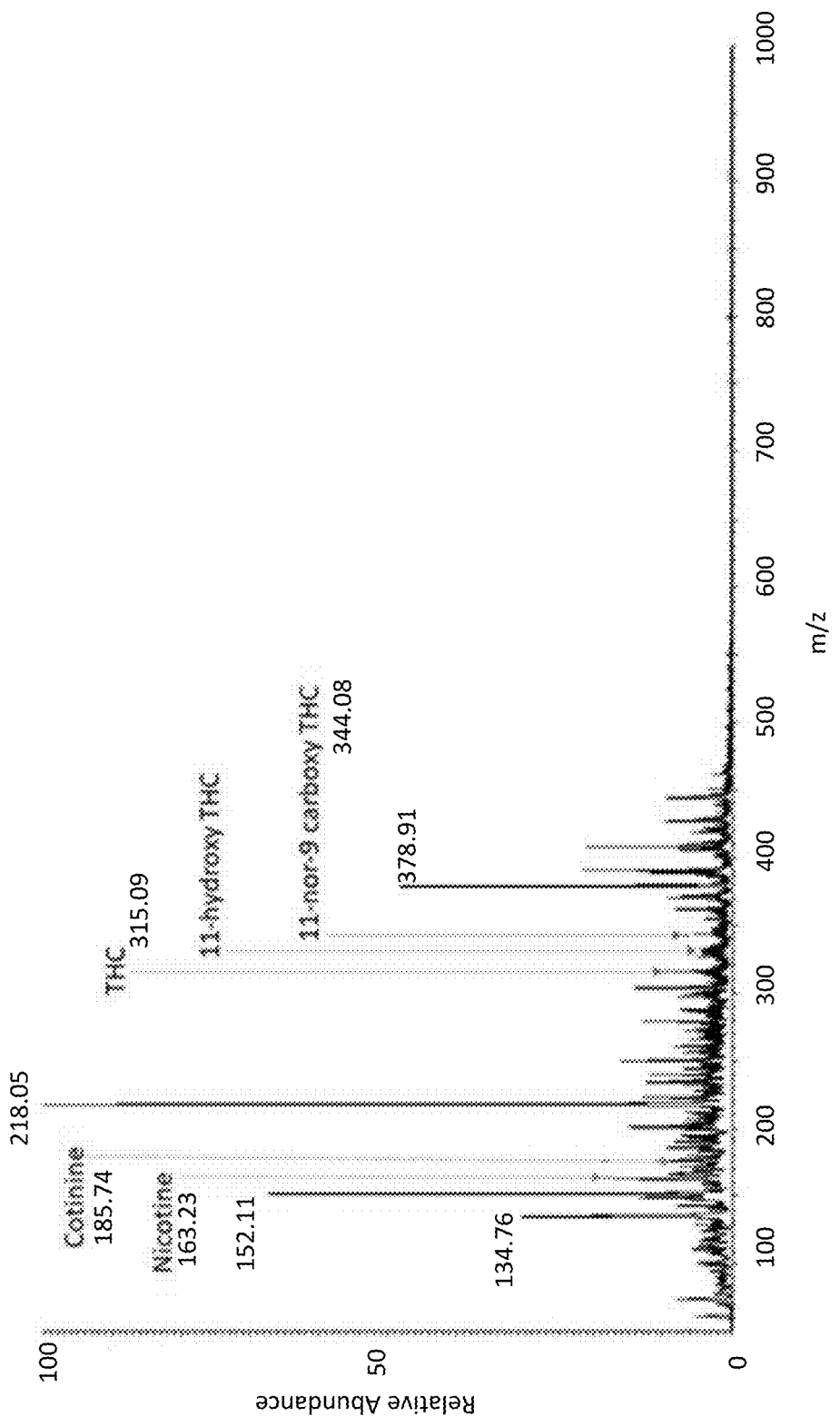
FIGS. 26-27 show the results for mass spectrum analyses for breath samples collected during an experiment conducted by the inventors.

Background spectra of the breath samples were first taken to determine all chemical species present and their relative abundances. Breath samples were then taken at subsequent time points. A mass spectrum for a breath sample taken at 90 min after consumption is shown in FIG. 26. Both THC (m/z 315) and nicotine (m/z 163) are visible, though they are not the most abundant species. The mass spectrum shows other compounds present either from breath or the environment. Notably, metabolites for THC (m/z 330 and 345) and nicotine (m/z 177) are also observable above baseline.

During calibration, the compensation voltage was fixed to 3.8V in the FAIMS device, the value at which the highest intensity THC signal transmitted through the FAIMS cell during the scan. The time needed to add and analyze each breath sample was approximately 10 seconds. While overall signal intensity is reduced by more than an order of magnitude using FAIMS, the signal/noise ratio is high enough such that a discrete signal is discernable by the detector.

Figure 27:
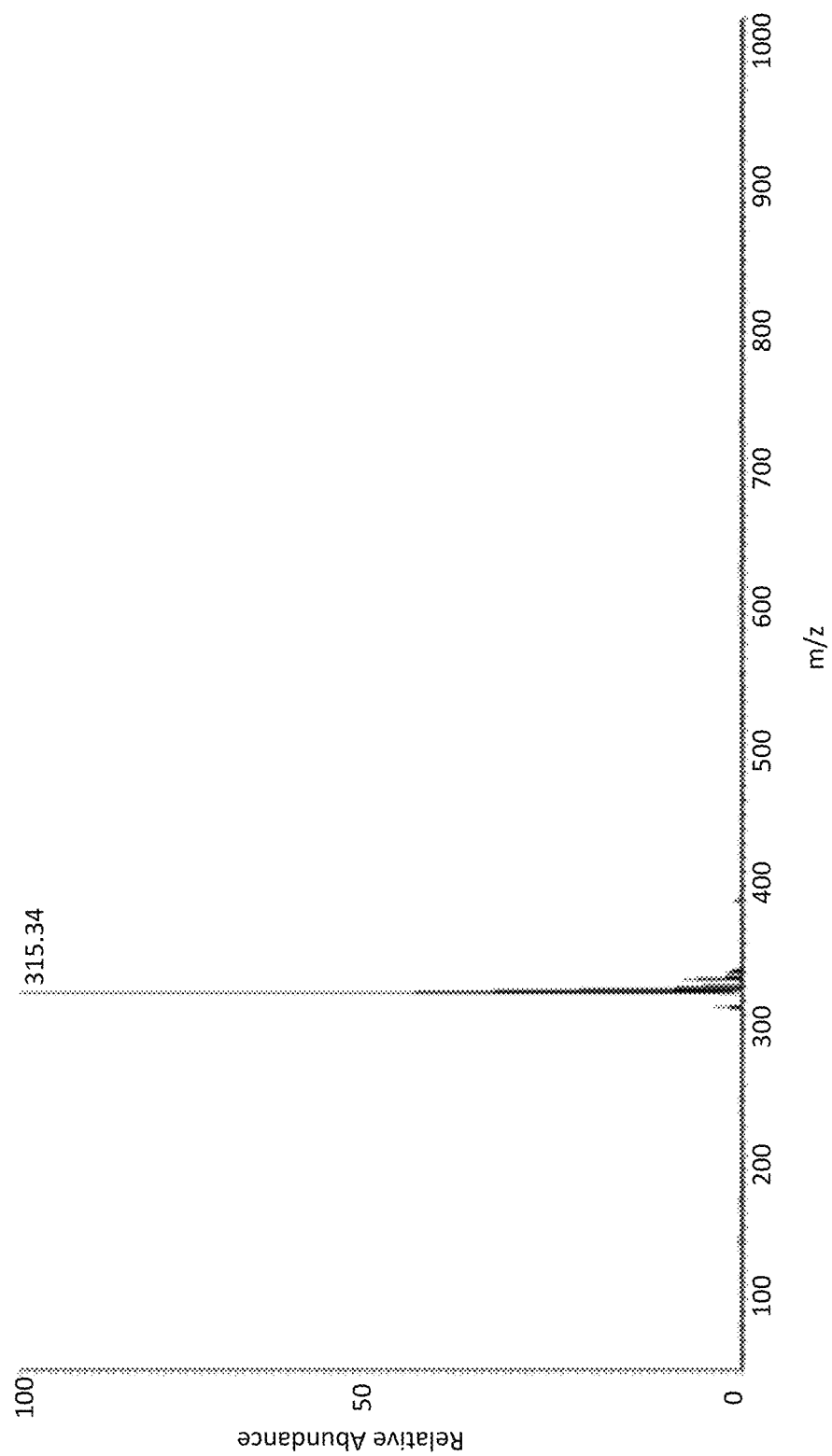

FIG. 27 is a mass spectrum showing transmission of THC (m/z 315) at a fixed FAIMS compensation voltage of 6.3V at DV 525V @ 1100 kHz for the same breath sample as shown in FIG. 26, i.e. FIG. 27 shows the same breath sample as in the previous figure, but with the FAIMS engaged. As with the standards, THC was fully resolved from nicotine, despite nicotine being present at higher relative abundance. The most abundant ion present in the example mass spectrum is over 1000× higher than that of THC, yet it is filtered out completely by FAIMS in FIG. 26, along with any other background ions that could possibly result in a device false positive.

The results of this example demonstrate that the experimental FAIMS system as described herein was calibrated using analyte standards and used to immediately analyze breath samples taken onsite for the presence of THC. The system was able to detect and discern the THC from a realistic dose of cannabis even as long as 90 minutes after consumption, which correlates with the theoretical window of detection. THC is far from the most abundant compound present in breath following cannabis use, especially when other compounds, such as nicotine, are also consumed. Sample size was only 5 to 7 breaths, and sampling and analysis time is much shorter (<1 min) than existing methods. Results can be obtained in the field via an onboard detector (though for purposes of this example, these responses were validated by mass spectrometry to confirm the identity of the observed peaks). This example shows that such a device is potentially useful for the detection of cannabis recency of use.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are consistent with the broadest interpretation of the specification as a whole.

The invention claimed is:

1. A system for detecting a target substance among a plurality of substances released from a source, the system comprising:
    an inlet for receiving the plurality of substances from the source;
    an ionization module downstream of the inlet, the ionization module operative at atmospheric pressure to ionize at least a portion of the plurality of substances received through the inlet to produce a plurality of ionized substances that travel along a linear flow path from a point where the plurality of ionized substances are ionized;
    a focusing module downstream of the ionization module;
    a FAIMS cell downstream of the focusing module with an entry to the FAIMS cell positioned along the linear flow path; and
    a gas inlet port provided at the focusing module for introducing a flow control gas into the system to provide an upstream fluid flow in the vicinity of the ionization module,
    wherein the focusing module is operative at atmospheric pressure to exert an axial component of force to draw the plurality of ionized substances into the focusing module and a radial component of force to guide the plurality of ionized substances to travel along the linear flow path through the focusing module and toward the entry of the FAIMS cell.

2. The system as defined in claim 1, wherein the linear flow path travelled by the plurality of ionized substances produced by the system from the point where the plurality of ionized substances are ionized to the FAIMS cell follows a principle axis.

3. The system as defined in claim 2, wherein the inlet, the ionization module, the focusing module and the FAIMS cell are linearly aligned along the principle axis.

4. The system as defined in claim 1, wherein the focusing module comprises a magnetic lens or an apparatus for exerting pneumatic and/or aerodynamic focusing forces.

5. The system as defined in claim 1, wherein the focusing module comprises one or more focusing electrodes capable of exerting electromagnetic focusing forces.

6. The system as defined in claim 5, wherein the focusing module comprises:
   a first electrode;
   a second electrode downstream of and axially spaced from the first electrode; and
   a third electrode downstream of and axially spaced from the second electrode.

7. The system according to claim 6, wherein the gas inlet port is provided between the first electrode and the second electrode.

8. The system according to claim 6, wherein a vacuum source is provided to draw air in a downstream direction through the system.

9. The system according to claim 8, wherein the flow control gas is introduced into the system at a rate which is greater than a suction rate of the vacuum.

10. The system according to claim 1, further comprising an outlet positioned upstream of the gas inlet port to allow unionized substances to exit the system.

11. The system according to claim 1, wherein the system further comprises a second gas inlet port for introducing a further portion of the flow control gas into the system, the second gas inlet port being positioned downstream of the FAIMS cell and upstream of a detector to decrease the rate of fluid flow through the FAIMS cell.

12. The system according to claim 1, wherein the FAIMS cell is a planar FAIMS cell.

13. The system according to claim 12, wherein the planar FAIMS cell comprises:
   first and second electrodes spaced by a gap to define a transit area therebetween, the transit area having opposing sides which define the entry and an exit of the planar FAIMS cell;
   a first voltage source coupled to the first electrode, the first voltage source operative to drive the first electrode with a first waveform; and
   a second voltage source coupled to the second electrode, the second voltage source operative to drive the second electrode with a second waveform,
   wherein the first and second waveforms are controlled to generate a time varying electric field in the transit area to separate the target substance from the plurality of substances as the plurality of substances travel from the entry to the exit of the planar FAIMS cell such that primarily or only the target substance exits the planar FAIMS cell, and
   wherein the first and second waveforms when combined result in the production of a net square waveform.

14. A method of separating a plurality of substances using FAIMS, the method comprising the steps of:
   introducing the plurality of substances into an inlet;
   passing the plurality of substances past an ionization module to ionize at least a first portion of the plurality of substances;
   causing the first portion of the plurality of substances to travel along a linear flow path from a point where the plurality of substances are ionized to a focusing module operating at atmospheric pressure;
   introducing a flow control gas into the system at the focusing module to create an upstream airflow at the focusing module;
   using an axial component of force provided by the focusing module to draw the first portion of the plurality of substances into the focusing module and a radial component of force provided by the focusing module to guide the first portion of the substances along the linear flow path through the focusing module and towards a FAIMS cell; and
   using the FAIMS cell to separate the first portion of the plurality of substances.

15. The method as defined in claim 14, wherein the forces provided by the focusing module comprise electromagnetic, magnetic, pneumatic and/or aerodynamic forces.

16. The method as defined in claim 14, wherein the forces provided by the focusing module comprise a force produced by a focusing electrode.

17. The method as defined in claim 14, wherein the FAIMS cell comprises a planar FAIMS cell, wherein a path of travel of the first portion of the plurality of substances through the FAIMS cell is along the linear flow path.

18. The method as defined in claim 16, wherein separation by the planar FAIMS cell is effected using a net square waveform.

19. The method as defined in claim 14, further comprising using the introduction of the flow control gas at the focusing module to force at least some of an unionized portion of the plurality of substances out of the flow path through an outlet.

20. The method as defined in claim 14, further comprising introducing a further flow control gas downstream of the FAIMS cell to decrease the rate of fluid flow through the FAIMS cell.

* * * * *